(12) United States Patent
Murad et al.

(10) Patent No.: US 11,007,058 B2
(45) Date of Patent: May 18, 2021

(54) VALVED AORTIC CONDUITS

(71) Applicant: Edwards Lifesciences Corporation, Irvine, CA (US)

(72) Inventors: Michael C. Murad, Corona, CA (US); Hilda Z. Fann, Santa Ana, CA (US); Mark Van Nest, Rancho Santa Margarita, CA (US); John X. Wang, Orange, CA (US); Derrick Johnson, Orange, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 310 days.

(21) Appl. No.: 16/052,775

(22) Filed: Aug. 2, 2018

(65) Prior Publication Data

US 2019/0046317 A1 Feb. 14, 2019

Related U.S. Application Data

(63) Continuation-in-part of application No. 14/850,829, filed on Sep. 10, 2015, now Pat. No. 10,058,425.
(Continued)

(51) Int. Cl.
*A61F 2/24* (2006.01)
*A61F 2/06* (2013.01)
*A61F 2/07* (2013.01)

(52) U.S. Cl.
CPC .......... *A61F 2/2445* (2013.01); *A61F 2/2412* (2013.01); *A61F 2/2418* (2013.01); *A61F 2/06* (2013.01); *A61F 2/07* (2013.01); *A61F 2/2409* (2013.01); *A61F 2210/0076* (2013.01); *A61F 2220/0075* (2013.01);
(Continued)

(58) Field of Classification Search
CPC ........ A61F 2/24; A61F 2/2445; A61F 2/2409; A61F 2/2427; A61F 2/2412; A61F 2/0095; A61F 2/06; A61F 2/064; A61F 2/2418; A61F 2/241; A61F 2310/00371; A61F 2310/00383; A61M 1/122; A61M 1/12;
(Continued)

(56) References Cited

U.S. PATENT DOCUMENTS 3,143,742 A 8/1964 Cromie
3,320,972 A 5/1967 High et al.
(Continued)

FOREIGN PATENT DOCUMENTS

EP 0125393 A1 11/1984
EP 0143246 A2 6/1985
(Continued)

*Primary Examiner* — Seema Mathew
(74) *Attorney, Agent, or Firm* — Guy Cumberbatch

(57) ABSTRACT

A valved conduit including a bioprosthetic aortic heart valve connected to a tubular conduit graft forming an ascending aorta. The conduit graft may attach to the heart valve in a manner that facilitates a redo operation in which the valve is replaced with another valve. A sewing ring may be pre-attached to the inflow end of the graft, and then the valve connected to a delivery holder advanced into the graft and secured to the sewing ring. Dry bioprosthetic valves coupled with conduit grafts sealed with a bioresorbable medium can be stored with the delivery holder.

23 Claims, 27 Drawing Sheets

Related U.S. Application Data which is a continuation of application No. PCT/US2014/030639, filed on Mar. 17, 2014.

(60) Provisional application No. 61/802,201, filed on Mar. 15, 2013.

(52) U.S. Cl.
CPC . *A61F 2230/0095* (2013.01); *A61F 2250/006* (2013.01); *A61F 2250/0039* (2013.01)

(58) Field of Classification Search
CPC .............. A61M 1/10; A61M 25/10185; A61M 1/1008; A61M 1/1098; A61M 1/1037
See application file for complete search history.

(56) References Cited

U.S. PATENT DOCUMENTS

| | | |
|---|---|---|
| 3,371,352 A | 3/1968 | Siposs et al. |
| 3,546,710 A | 12/1970 | Shumakov et al. |
| 3,574,865 A | 4/1971 | Hamaker |
| 3,755,823 A | 9/1973 | Hancock |
| 3,839,741 A | 10/1974 | Haller |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,692,164 A * | 9/1987 | Dzemeshkevich ... A61F 2/2412 623/2.14 |
| 4,705,516 A | 11/1987 | Barone et al. |
| 4,725,274 A | 2/1988 | Lane et al. |
| 4,747,848 A * | 5/1988 | Maini ...................... A61F 2/06 530/354 |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin |
| 5,032,128 A | 7/1991 | Alonso |
| 5,037,434 A | 8/1991 | Lane |
| 5,123,919 A * | 6/1992 | Sauter ...................... A61F 2/06 623/1.26 |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,488,769 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,614,097 A | 3/1997 | Bender et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,074,418 A | 6/2000 | Buchanan et al. |
| 6,081,737 A | 6/2000 | Shah |
| 6,083,179 A | 7/2000 | Oredsson |
| 6,090,140 A * | 7/2000 | Gabbay .................. A61B 17/11 623/2.1 |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |

(56) References Cited

U.S. PATENT DOCUMENTS

| | | |
|---|---|---|
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,299,638 B1 * | 10/2001 | Sauter ................. A61F 2/06 623/1.26 |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,352,554 B2 * | 3/2002 | De Paulis ............. A61F 2/06 623/1.24 |
| 6,371,983 B1 | 4/2002 | Lane |
| 6,375,620 B1 | 4/2002 | Oser et al. |
| 6,402,760 B1 | 6/2002 | Williamson, IV et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,460 B2 | 5/2005 | Spenser et al. |
| 6,908,461 B2 | 6/2005 | Cribier |
| 6,939,365 B1 | 9/2005 | Fogarty et al. |
| 7,011,681 B2 | 3/2006 | Vesely |
| 7,018,404 B2 | 3/2006 | Holmberg et al. |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,998,151 B2 | 8/2011 | St Goar et al. |
| 8,080,054 B2 * | 12/2011 | Rowe ................. A61F 2/844 623/1.26 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Larnbrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanicize et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159611 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0222675 A1 | 10/2005 | Sauter |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Saiahieh et al. |
| 2006/0074484 A1 | 4/2006 | Huber |
| 2006/0085060 A1 * | 4/2006 | Campbell ............... A61F 2/06 623/1.26 |
| 2006/0095125 A1 | 5/2006 | Chinn et al. |
| 2006/0122634 A1 | 6/2006 | Ino et al. |

(56) References Cited

U.S. PATENT DOCUMENTS

| | | |
|---|---|---|
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0179604 A1 | 6/2007 | Lane |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0219630 A1 * | 9/2007 | Chu ..................... A61F 2/2412 623/2.11 |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0254273 A1 | 11/2007 | LaFrance et al. |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0082161 A1 | 4/2008 | Woo |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0192599 A1 | 7/2009 | Lane et al. |
| 2010/0049313 A1 | 2/2010 | Alon et al. |
| 2010/0274351 A1 | 10/2010 | Rolando et al. |
| 2011/0054598 A1 | 3/2011 | Johnson |
| 2012/0010697 A1 * | 1/2012 | Shin ..................... A61F 2/2415 623/1.26 |
| 2012/0132547 A1 * | 5/2012 | Salahieh ............... A61F 2/0095 206/210 |
| 2013/0172991 A1 | 7/2013 | Rolando et al. |
| 2013/0184814 A1 * | 7/2013 | Huynh .................. A61F 2/2412 623/2.36 |

FOREIGN PATENT DOCUMENTS

| | | |
|---|---|---|
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 0245933 A2 | 6/2002 |
| WO | 2007008371 A2 | 1/2007 |
| WO | 2009137805 A1 | 11/2009 |

* cited by examiner

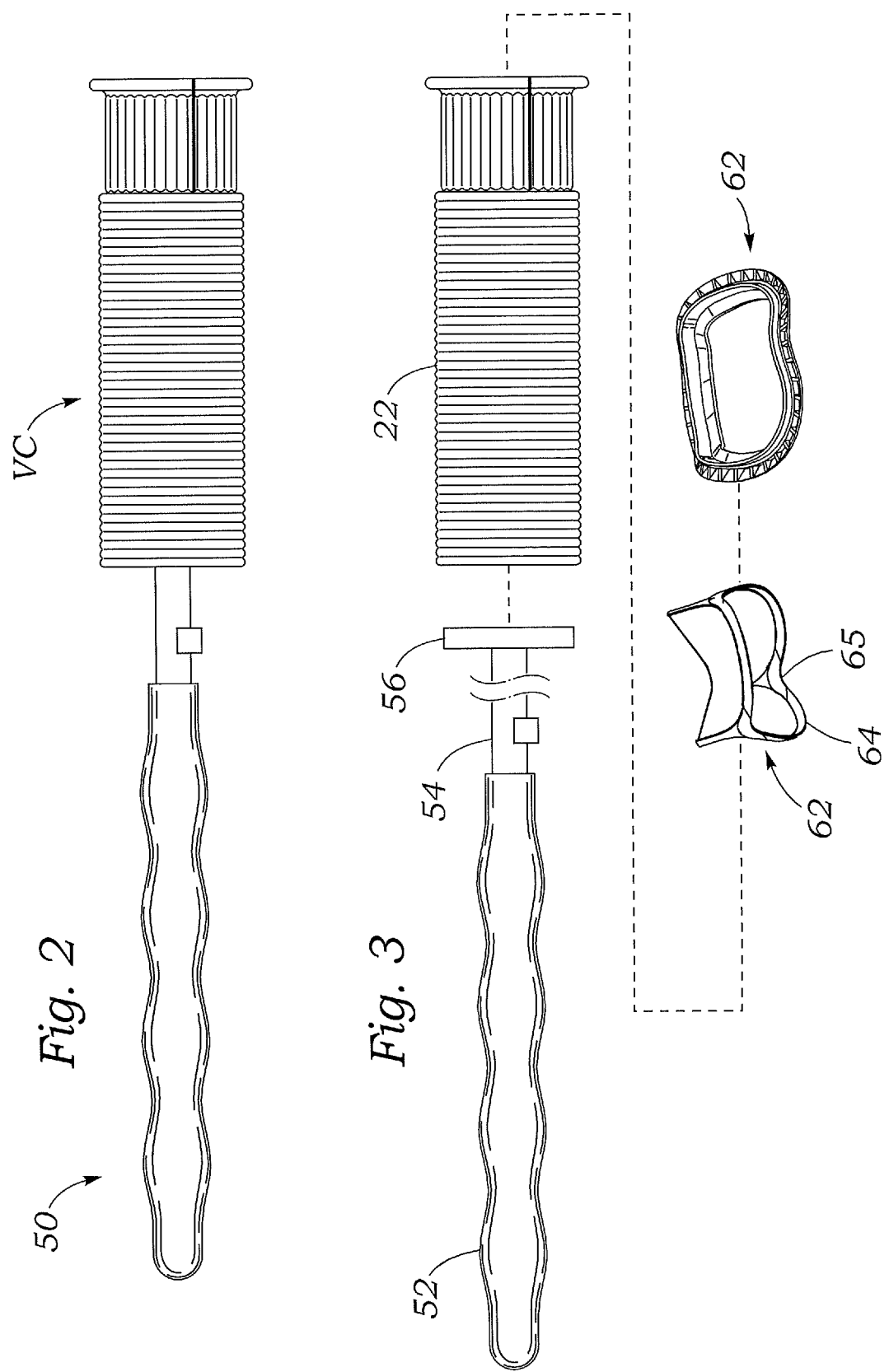

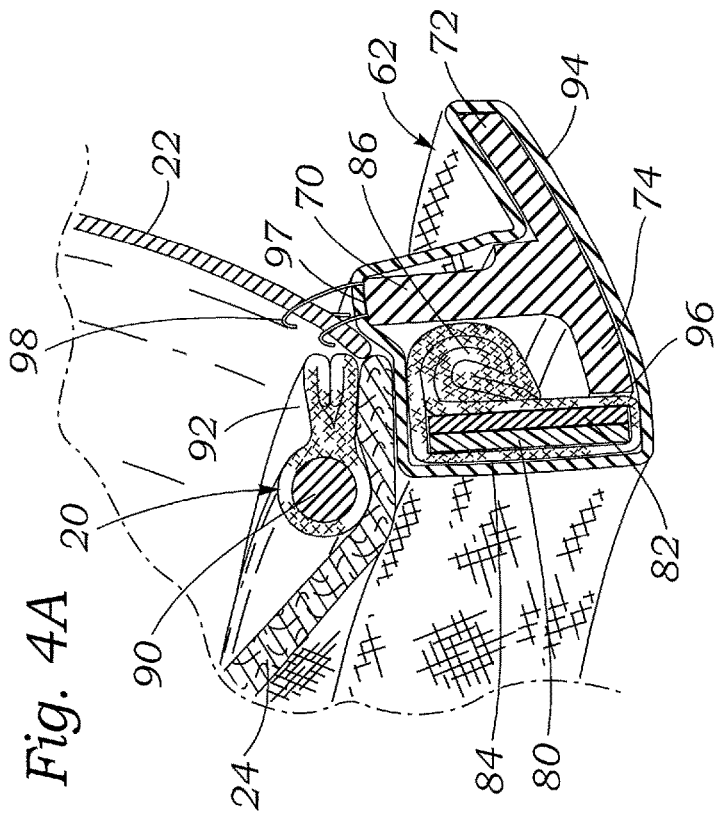
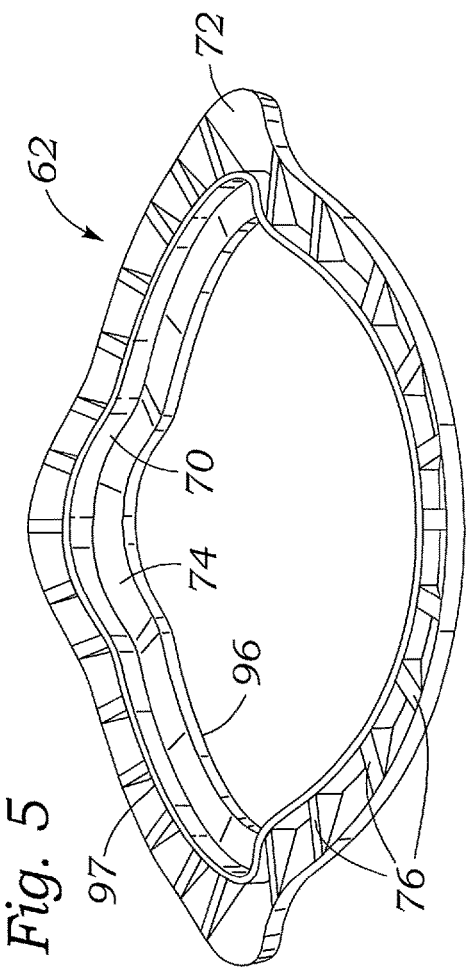
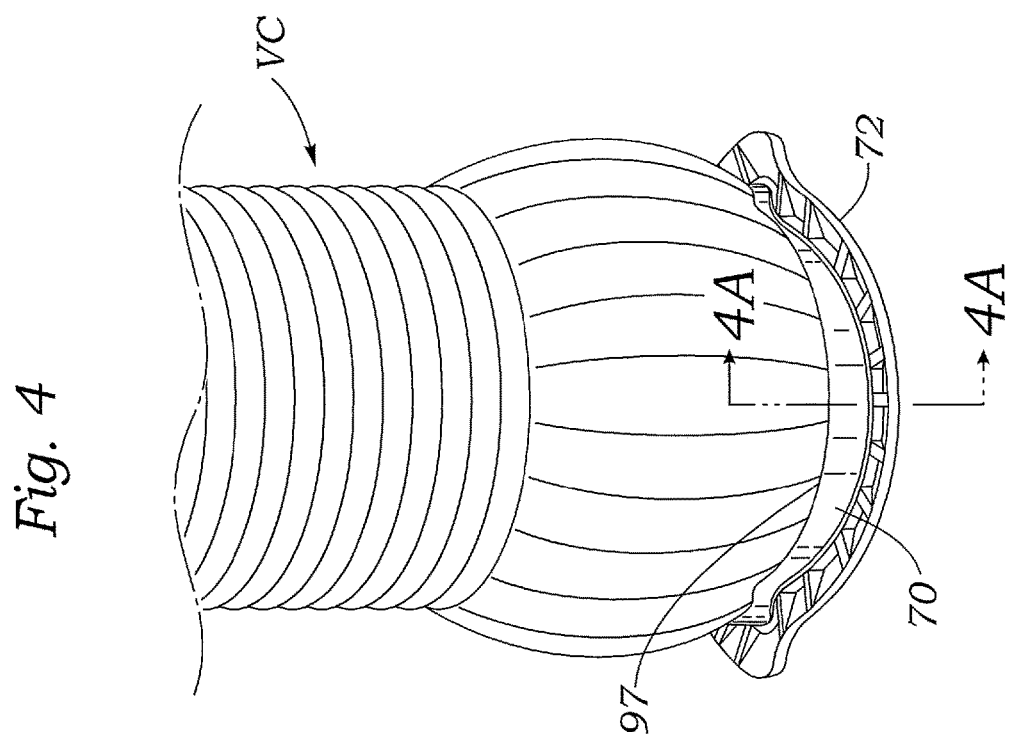

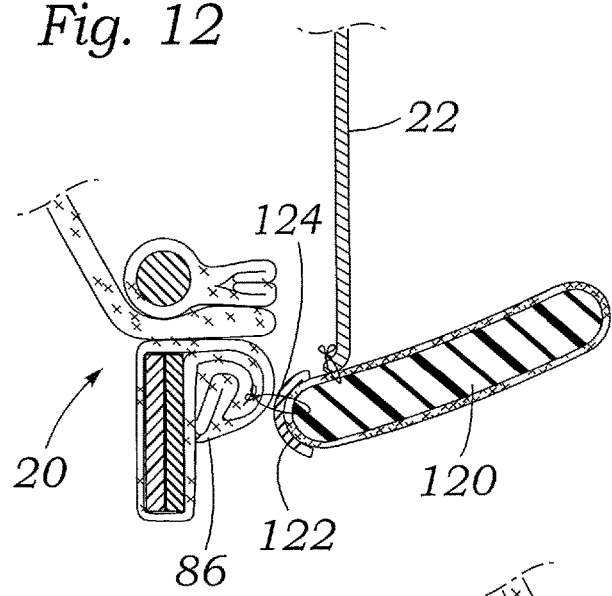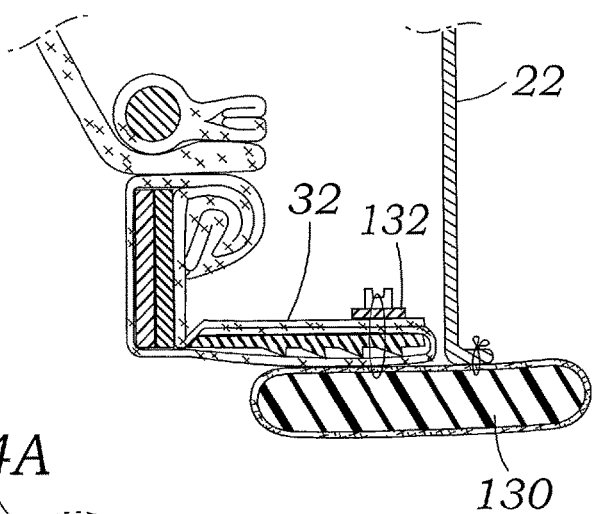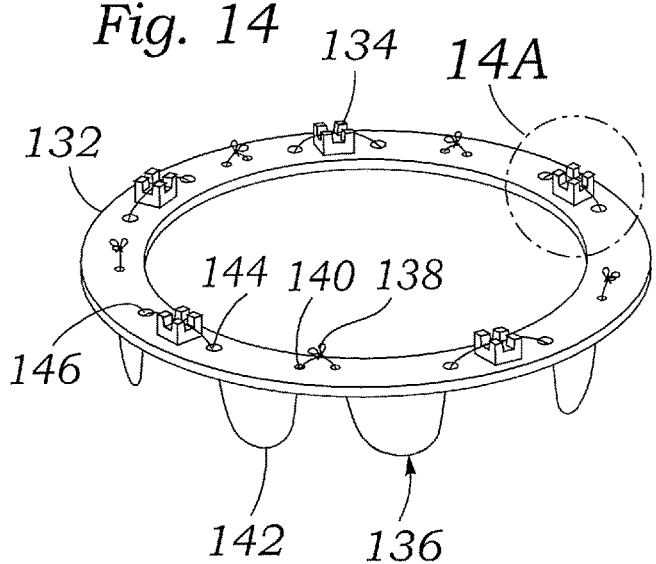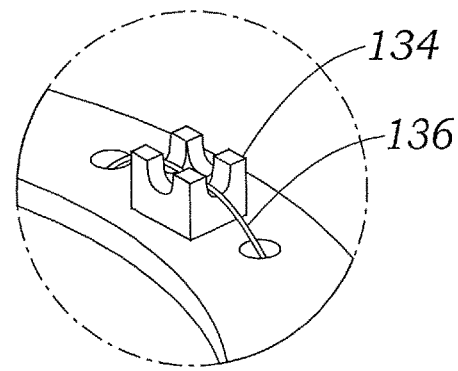

Fig. 18A
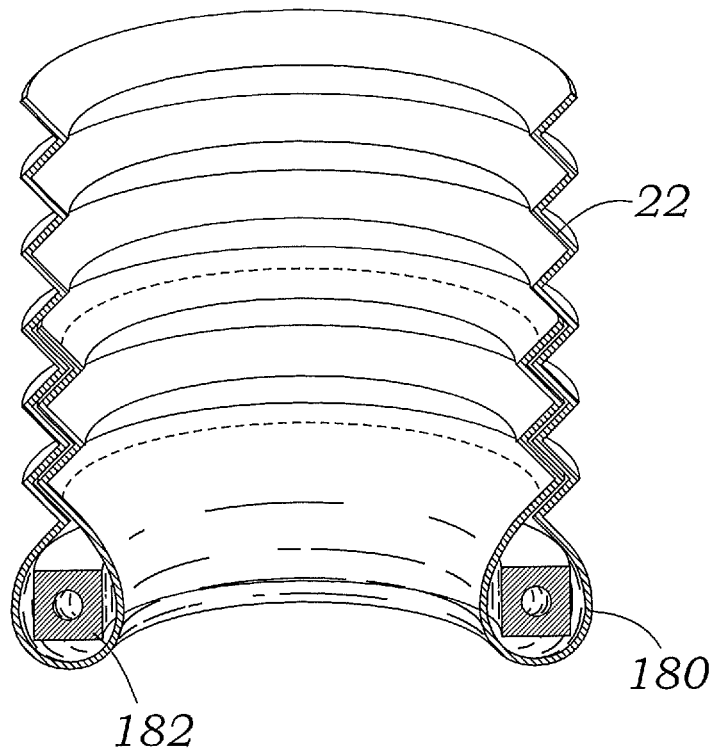
Fig. 18B
Fig. 18C
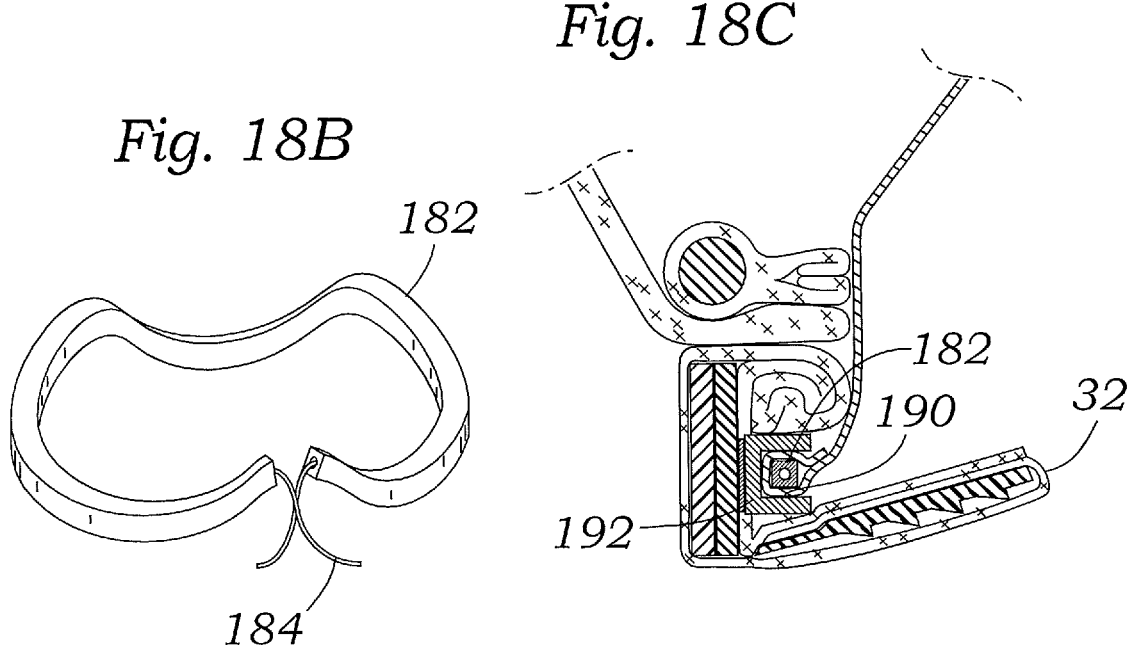

Fig. 25
Fig. 26
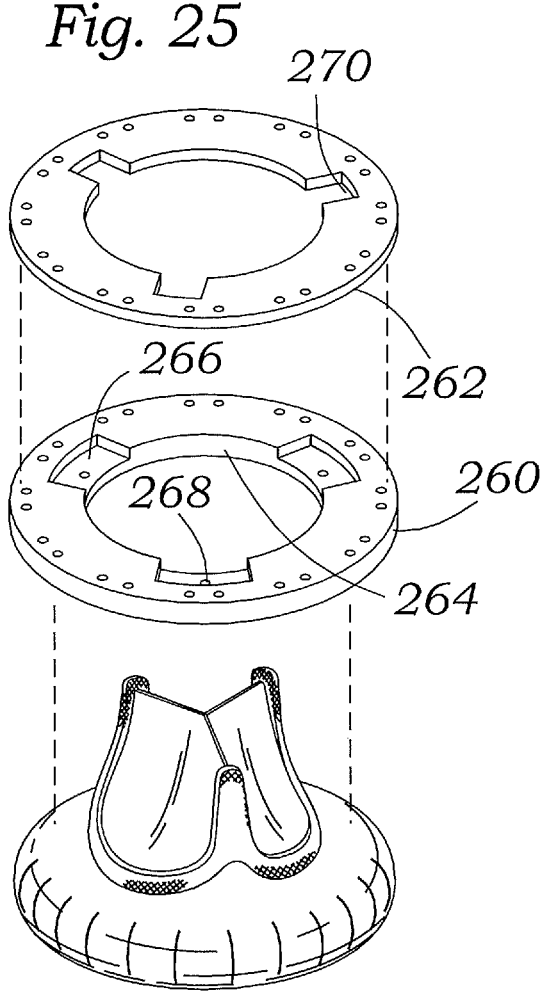
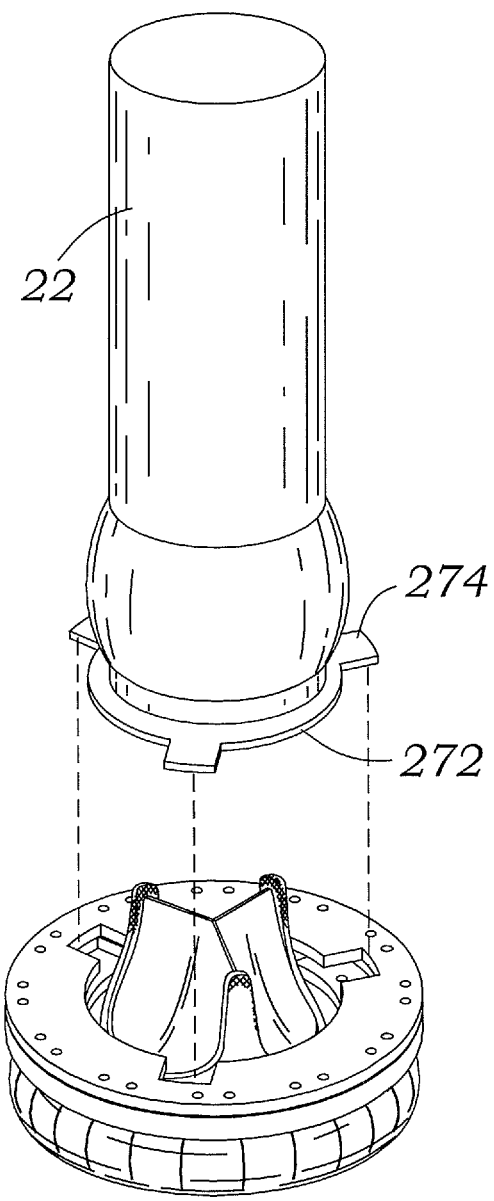
Fig. 26A
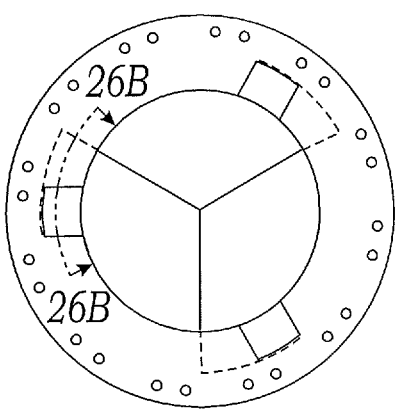
Fig. 26B
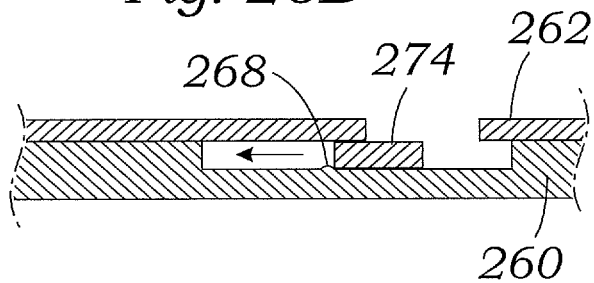

Fig. 28
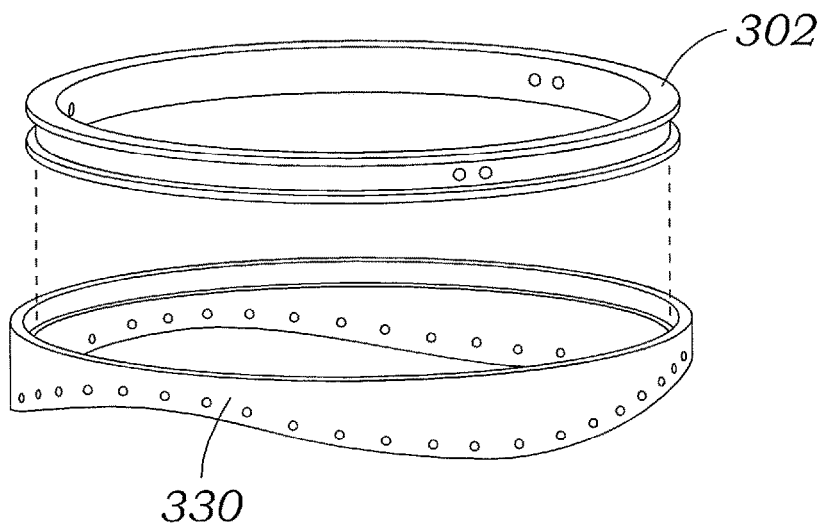
Fig. 29B
Fig. 29A
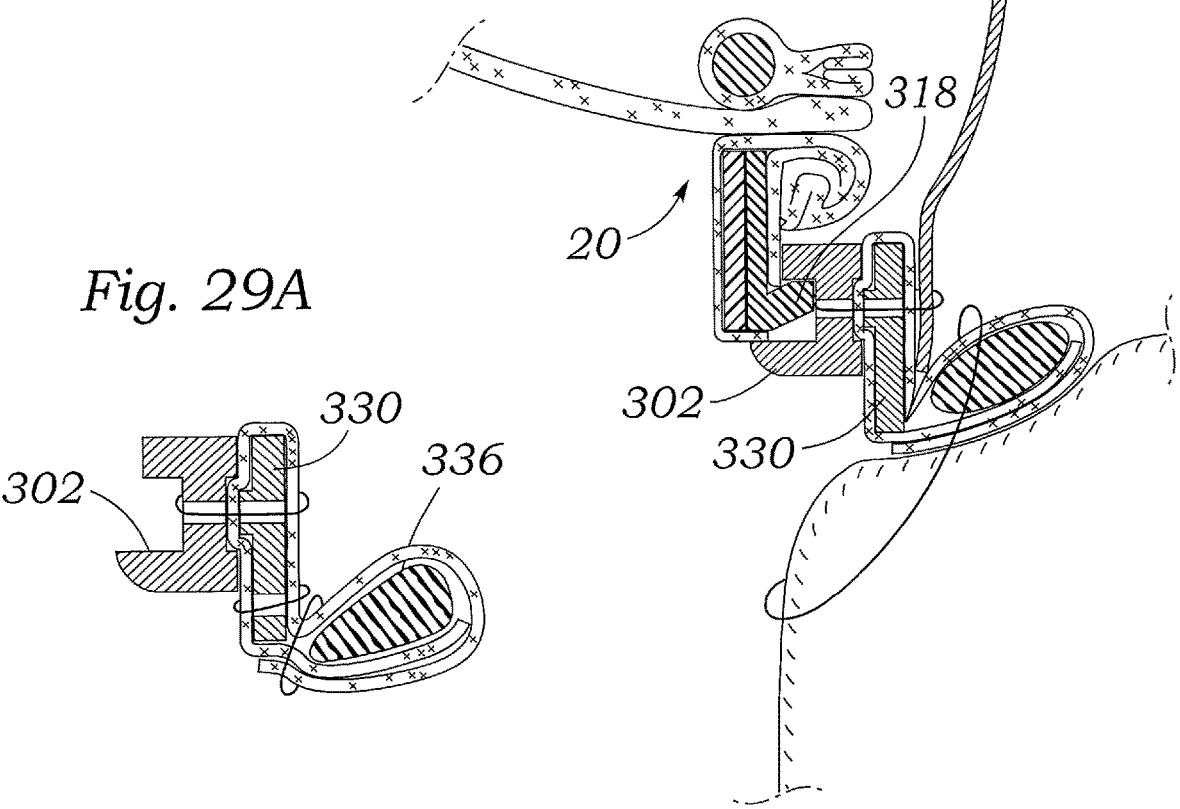

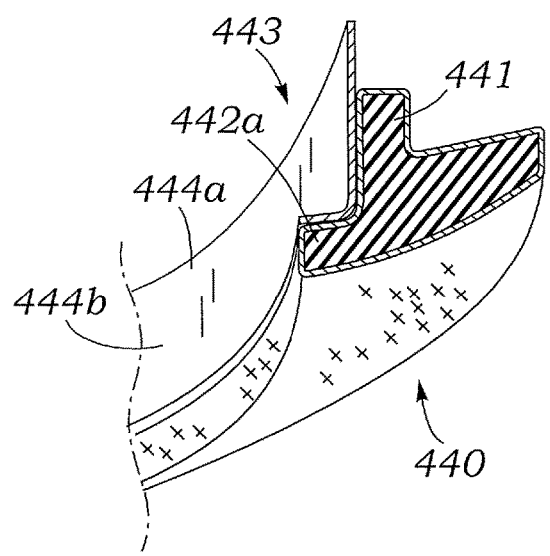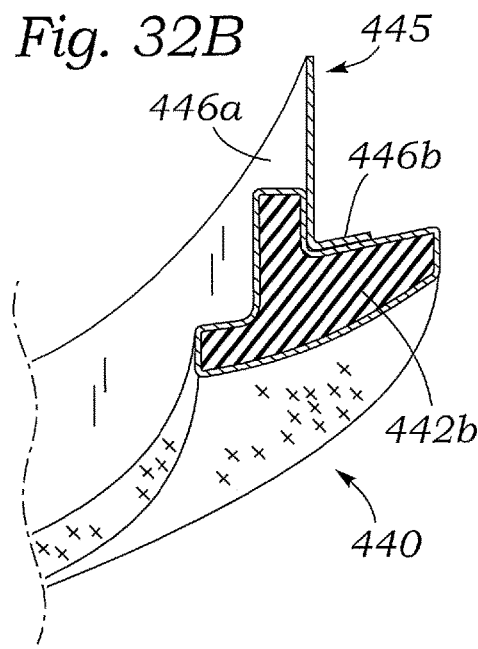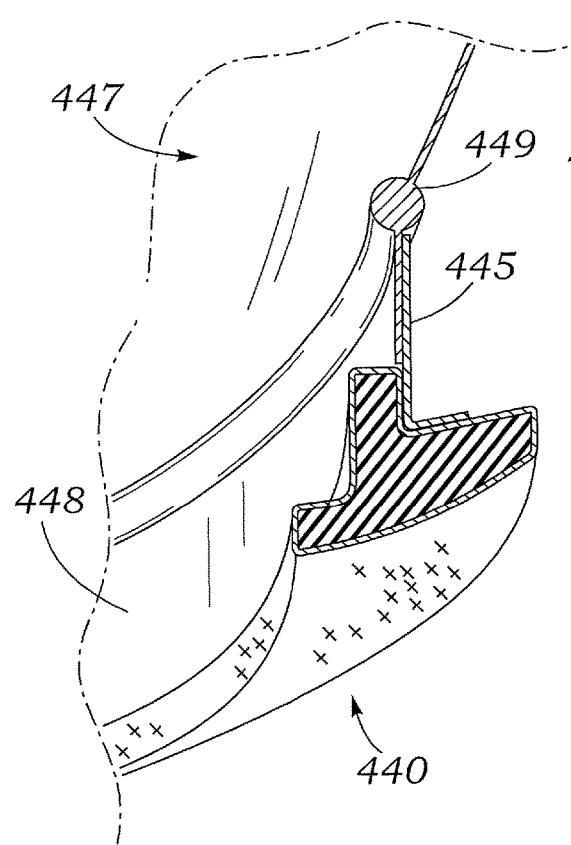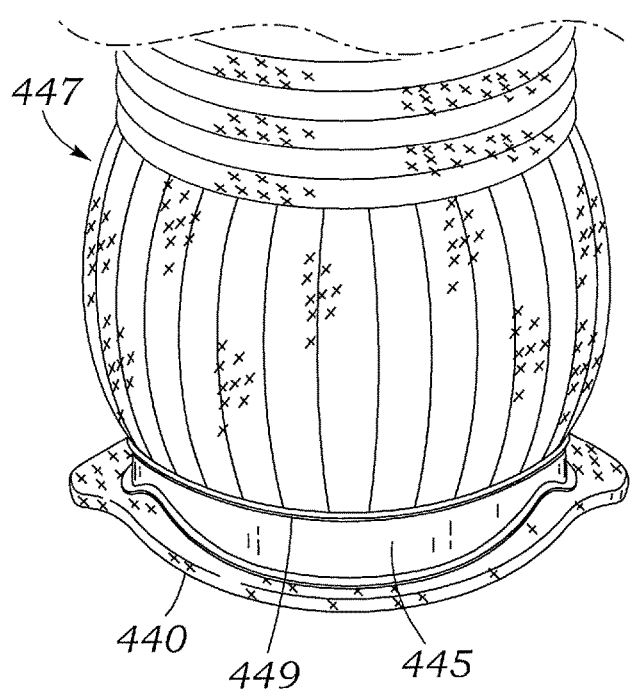

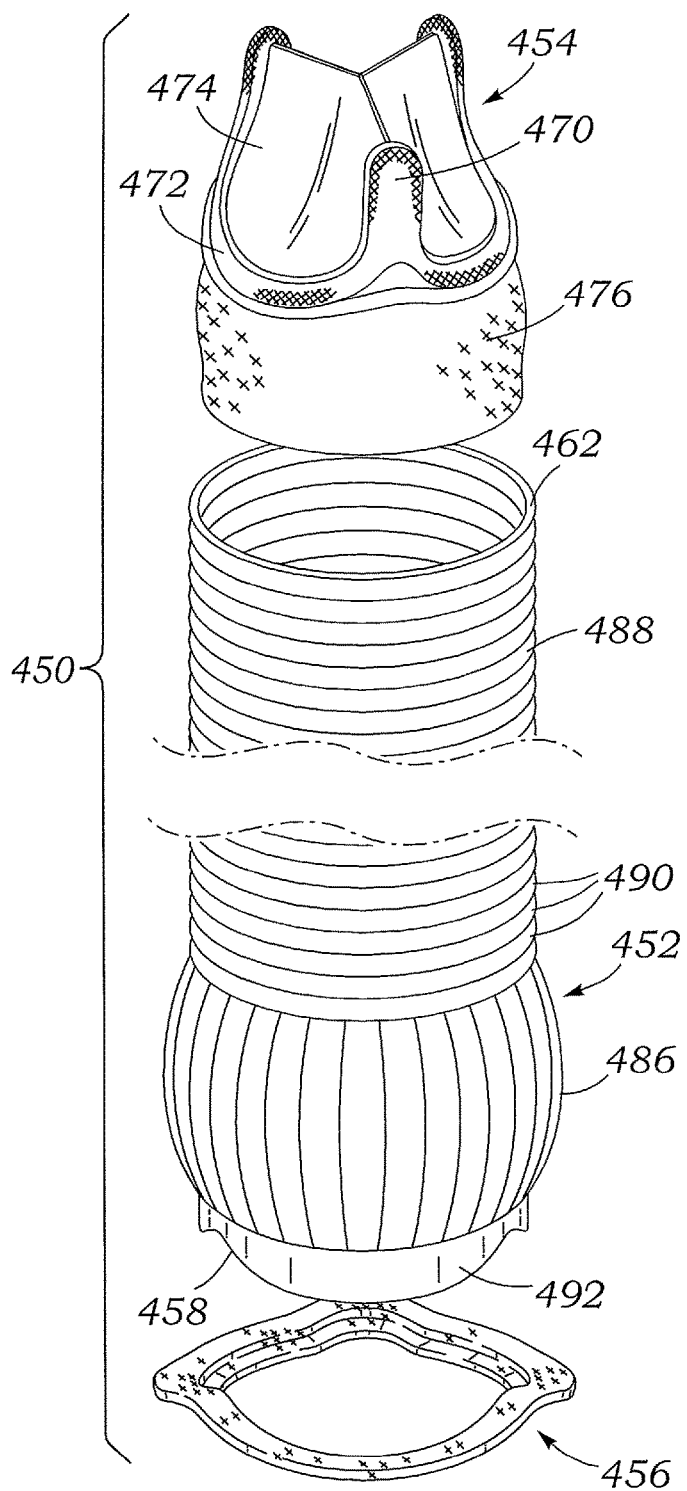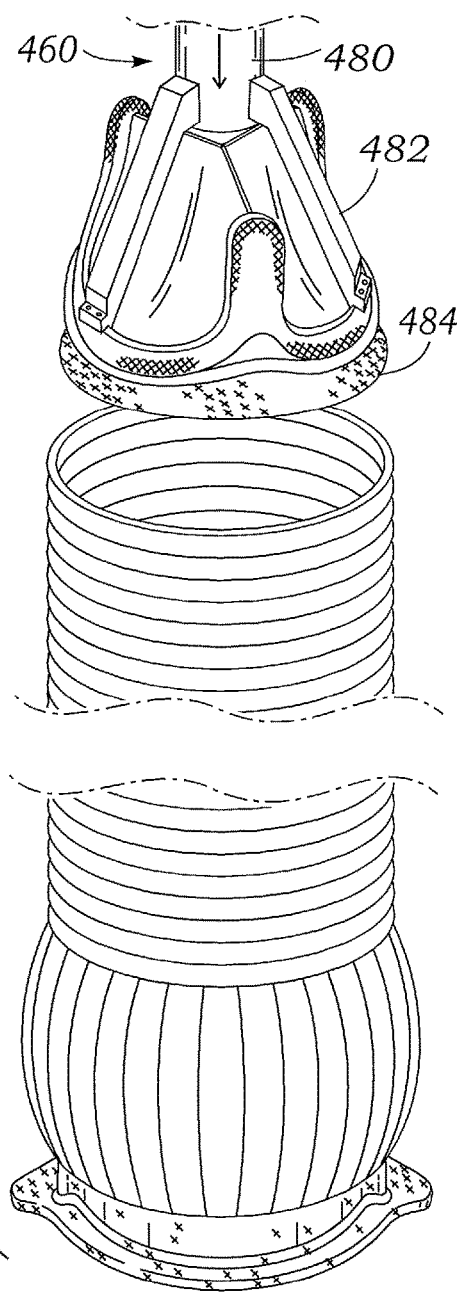

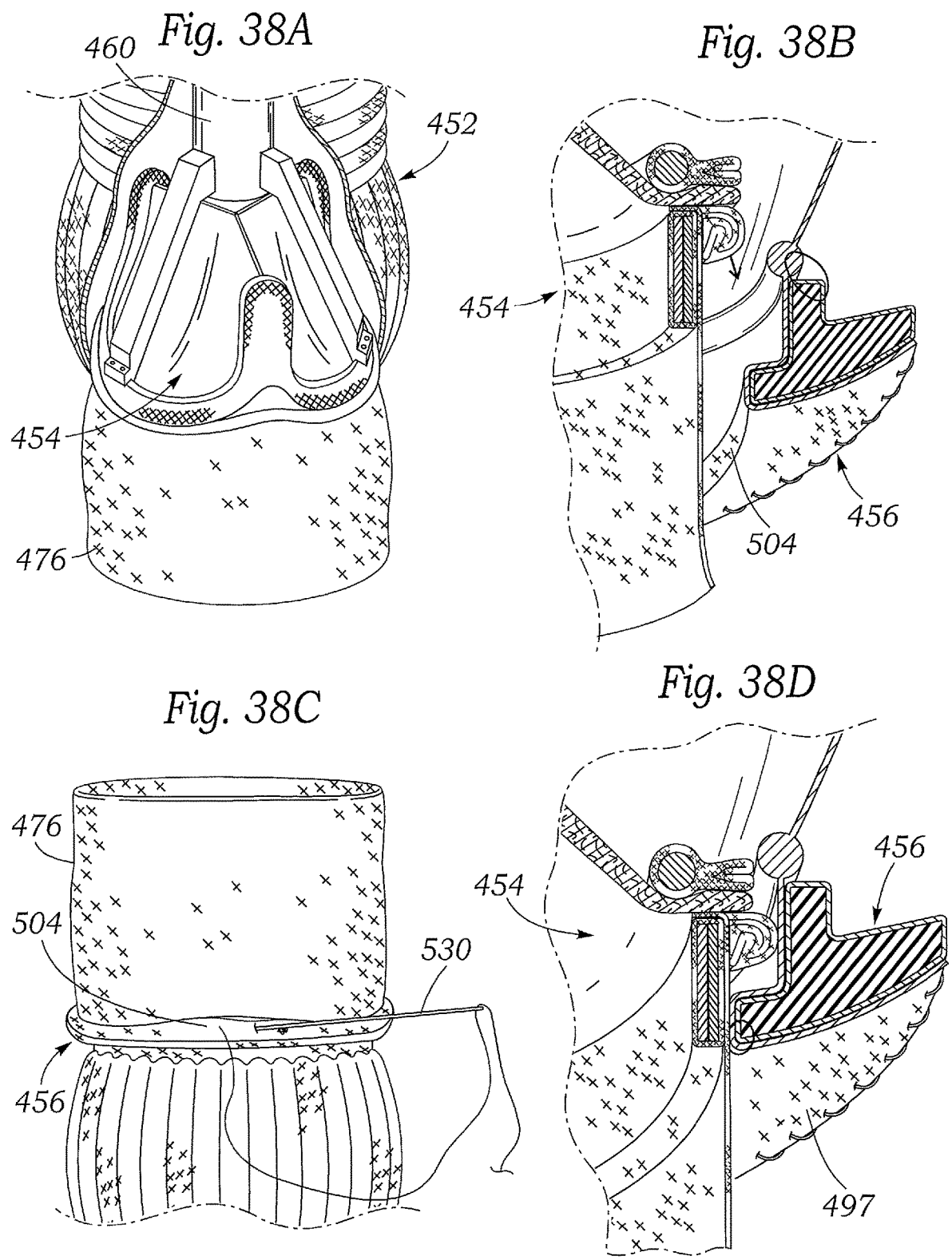

VALVED AORTIC CONDUITS

RELATED APPLICATIONS

The present application is a continuation-in-part of U.S. application Ser. No. 14/850,829, filed Sep. 10, 2015, which is a continuation of PCT/US2014/030639, filed Mar. 17, 2014, which claims priority under 35 U.S.C. § 119 to U.S. Provisional Application Ser. No. 61/802,201, filed Mar. 15, 2013. The foregoing applications are each incorporated by reference herein.

FIELD OF THE INVENTION

The present invention generally relates to a prosthetic heart valve assembled with a flow conduit and, more particularly, to a pre-assembled aortic heart valve and aortic conduit that facilitates a redo operation wherein the valve is replaced with another valve.

BACKGROUND OF THE INVENTION

Heart valve disease continues to be a significant cause of morbidity and mortality, resulting from a number of ailments including rheumatic fever and birth defects. Cardiovascular disease is the number one cause of death, killing more than 600,000 Americans each year. According to the American Heart Association, more than five million Americans are diagnosed with heart valve disease each year. Heart valve disease can occur in any single valve or a combination of the four valves, but diseases of the aortic and mitral valves are the most common, affecting more than five percent of the population. An estimated 85,000 aortic valve replacement procedures are performed every year in the U.S. Worldwide, approximately 300,000 heart valve replacement surgeries are performed annually. About one-half of these patients receive bioprosthetic heart valve replacements, which utilize biologically derived tissues for flexible fluid occluding leaflets.

Prosthetic heart valves may be implanted independently in one of the orifices or annuluses of the heart, or may be coupled to a flow conduit which extends in line with the valve a predetermined distance. In the so-called Bentall procedure the combined pathology of ascending aorta and aortic valve are replaced. There are a number of combined conduits and valves on the market. Prior bioprosthetic valved conduits, as with bioprosthetic heart valves, are stored in a liquid preserving solution, and thus the conduits are formed of woven polyester without a bioresorbable sealant. Although such conduits are suitable in certain situations, and tend to seal relatively quickly in the body from tissue ingrowth, too much blood can initially seep through their walls after implant which may be detrimental. Uncoated fabric such as polyethylene terephthalate (PET) has a high leakage rate, and thus the surgeon needs to pre-clot the graft with patient's blood before use. Nevertheless, such grafts still produce unacceptable leaking. Others have proposed using a non-bioresorbable sealant layer, such as silicone in U.S. Patent Publication No. 2008/0147171 to Ashton, et al., published Jun. 19, 2008, but such layered conduits tend to be relatively thick walled and not very flexible, and so are not preferred.

Consequently, some surgeons prefer conduits or grafts in which porous tubular structures such as woven polyester (e.g., Dacron) are impregnated with bioresorbable materials such as gelatin, collagen or albumin. These conduits are not porous initially, and thus prevent blood loss, but the sealant medium eventually degrades by hydrolysis when exposed to water after implant and are replaced by natural tissue ingrowth. Gelatin in the graft can also be treated in such a way as to cause cross links to form between the amino groups present in the gelatin molecules, which renders the gelatin more resistant to hydrolysis. Methods of forming such grafts are seen in U.S. Pat. No. 4,747,848 to Maini, issued May 31, 1988.

Unfortunately, it is not possible to pre-assemble conduits or grafts sealed using bioresorbable materials with bioprosthetic heart valves because of storage complications. That is, the liquid sterilant in which tissue valves are stored will eventually wash the bioresorbable sealing medium (gelatin, collagen, albumin, etc.) out of the permeable conduit material. Because of the benefits of using sealed conduits or grafts and the positive attributes of bioprosthetic heart valves, some surgeons couple the two components together at the time of surgery—post-storage. That is, technicians in the operating theater connect the sealed conduit which has been stored dry to the bioprosthetic heart valve which has been stored wet. Such assemblies can be seen in U.S. Pat. No. 8,512,397 to Rolando, et al., issued Aug. 20, 2013, and in U.S. Pat. No. 7,575,592 to Woo, et al., issued Aug. 18, 2009. The sealed conduit may be sewn to the sewing ring of the bioprosthetic heart valve, or some other form of quick-connect coupling can be provided, such as seen in U.S. Patent Publication No. 2006/0085060 to Campbell, published Apr. 20, 2006.

Once implanted, many valved conduits require a valve re-replacement, or "redo" procedure, such as if the bioprosthetic leaflets calcify. Unfortunately, many of the prior valved conduit designs are so integrated that the entire assembly must be removed, rather than just the non-functioning valve.

Despite these advances, there is a need for a valved conduit having a bioprosthetic tissue valve which is simpler to implant and which facilitates replacement of the valve if necessary.

SUMMARY OF THE INVENTION

A valved conduit including a bioprosthetic aortic heart valve connected to a tubular conduit graft forming an ascending aorta. The conduit graft attaches to the heart valve in a manner that facilitates a redo operation in which the valve is replaced with another valve. Various connection configurations are provided, some in which the conduit graft is sewn to the heart valve sewing ring, some in which there are two sewing rings, and some which utilize more mechanical snap-fit or locking ring connections.

The present application discloses a valved conduit including a bioprosthetic heart valve and a tubular conduit, preferably sealed with a bioresorbable material. The bioprosthetic heart valve may have prosthetic tissue that has been treated such that the tissue may be stored dry for extended periods without degradation of functionality of the valve. The bioprosthetic heart valve may have separate bovine pericardial leaflets or a whole porcine valve. The heart valve may be sewn within the conduit, sewn to the end of the conduit or coupled thereto with a snap-fit connection to limit handling of the two treated components and provide a hemostatic seal with minimal assembly complexity. Preferably the attachment configuration facilitates a redo operation in which the valve can be easily excised from within the graft and replaced.

In one preferred embodiment, a valved conduit comprises a subassembly of a conduit graft and an annular sewing ring.

The conduit graft includes a longitudinal tubular portion between an upper end and a lower end, the lower end having a collar portion. The sewing ring comprising an inner core and an outer fabric covering, the sewing ring being positioned adjacent the lower end of the conduit graft whereby the collar portion contacts and is secured to an inner wall of the annular sewing ring. The subassembly of the conduit graft and sewing ring is independently leak tested. A prosthetic heart valve in the valved conduit has an inner support frame covered with fabric and defining a flow orifice and a plurality of leaflets extending inward from the support frame to ensure one-way blood flow through the heart valve. The heart valve is positioned within the lower end of the conduit graft and the fabric covering the support frame extends downward in a tubular segment and is folded radially outward underneath the subassembly of the conduit graft and sewing ring and secured thereto with sutures. Finally, a holder attaches to the heart valve and extends from the heart valve out of the upper end of the conduit graft.

In the valved conduit described above, the collar portion may have an undulating shape around its circumference with peaks and valleys, and the sewing ring also has an undulating shape around its circumference with peaks and valleys, wherein the peaks and valleys of the collar portion align with the peaks and valleys of the sewing ring. The conduit graft may be secured to the sewing ring using sutures, by welding, or using an intermediate band which is secured to both the conduit graft and sewing ring. The heart valve leaflets are desirably made of bioprosthetic tissue, and the conduit graft preferably comprises a tubular matrix impregnated with gelatin. The heart valve leaflets are more preferably formed of bovine pericardium that has been cross-linked using glutaraldehyde or other aldehyde containing agents, treated with a capping agent, and is dehydrated with a glycerol solution.

A method of assembling a valved conduit disclosed herein, comprises the following steps:
  forming a subassembly of a conduit graft and an annular sewing ring, the conduit graft comprising a longitudinal tubular portion between an upper end and a lower end, the lower end having a collar portion, the sewing ring comprising an inner core and an outer fabric covering, the step of forming comprising positioning the sewing ring adjacent the lower end of the conduit graft so that the collar portion contacts an inner wall of the annular sewing ring and securing the collar portion thereto;
  leak testing the subassembly of the conduit graft and sewing ring;
  providing a prosthetic heart valve having an inner support frame covered with fabric and defining a flow orifice and a plurality of leaflets extending inward from the support frame to ensure one-way blood flow through the heart valve, the fabric covering the support frame extending downward in a tubular segment;
  attaching a holder to the heart valve; and
  positioning the heart valve within the lower end of the leak tested subassembly of the conduit graft and sewing ring and folding the tubular segment of the fabric covering radially outward underneath the subassembly and secured the tubular segment thereto with sutures, the holder having a length sufficient to extend from the heart valve out of the upper end of the conduit graft.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 2 is an elevational view of a valved conduit of the present application coupled to a delivery handle;

FIG. 3 is an exploded view of the delivery handle and valved conduit showing primary components of the bioprosthetic heart valve;

FIG. 4 is a perspective view of the lower or inflow end of the valved conduit illustrating an exemplary sewing ring minus an outer fabric covering, and FIG. 4A is a radial sectional view through a lower end of the valved conduit taken through a cusp portion of the exemplary sewing ring, this time showing the outer fabric covering;

FIG. 5 is a perspective view of the exemplary sewing ring;

FIG. 12 is a radial sectional view through a lower end of the valved conduit wherein the conduit attaches to a sewing band which, in turn, attaches to a fabric tab of the heart valve through a protective cap;

FIG. 13 is a radial sectional view through a lower end of the valved conduit wherein the conduit attaches to the secondary sewing ring which, in turn, attaches to a primary sewing ring of the heart valve via a ring adapter having cutting guides;

FIG. 14 is a perspective view of the ring adapter from FIG. 13 schematically showing the path of sutures used to secure the ring to the valved conduit, and FIG. 14A is an enlarged view of one cutting guide from the top of the ring adapter;

FIG. 18A is a longitudinal sectional view through a lower end of a conduit having a tubular hem enclosing a locking ring, while FIG. 18B illustrates an exemplary form of a locking ring and FIG. 18C is a radial sectional view through a lower end of a valved conduit in which the locking ring at the bottom end of the conduit is held within an outwardly opening channel secured to the heart valve;

FIG. 19A is a radial sectional view through a lower end of a valved conduit showing a locking ring hemmed to the lower end of the conduit and secured within an inwardly opening locking channel secured to the heart valve, while

FIG. 25 is an exploded perspective view of a prosthetic heart valve having a pair of coupling rings attached thereto;

FIG. 26 is an exploded perspective view of a conduit graft having a locking ring on a lower end above the assembled prosthetic heart valve of FIG. 25, and FIGS. 26A and 26B are plan and sectional views illustrating the engagement between the locking ring and the coupling rings of the prosthetic heart valve;

FIG. 28 illustrates the locking ring of the embodiment of FIGS. 27A-27C and an outer anchoring member that forms a part of the lower end of a conduit graft;

FIG. 29A is a radial sectional view of the engagement between the sewing ring cuff and an exemplary outer anchoring ring having the anchoring member therein, and FIG. 29B is a radial sectional view showing the assembly of FIG. 28 connected to a conduit graft, and also illustrating the heart valve engaging the sewing ring cuff;

FIG. 30 is a perspective view of a still further connection arrangement between a conduit graft and a prosthetic heart valve utilizing an intermediate band attached to the graft and having a crown-shaped lower edge while

FIGS. 32A-32D are sectional and perspective views of one embodiment of a subassembly of a conduit graft and annular sewing ring connected together via an intermediate band;

FIG. 33A is a perspective exploded view of an alternative configuration of a valved conduit system;

FIG. 33B is a perspective view showing a prosthetic heart valve being coupled to a sewing ring/conduit graft subassembly to form the valved conduit system;

FIGS. 38A-38D are perspective and sectional views of several preliminary steps for coupling the prosthetic heart valve to the sewing ring/conduit graft subassembly of FIG. 33A;

DETAILED DESCRIPTION OF THE PREFERRED EMBODIMENTS

Described herein are a number of two-piece valved conduits including a prosthetic heart valve and a conduit graft that facilitate valve redo operations. That is, the heart valve within the valved conduit sometimes becomes calcified and must be replaced. The combinations disclosed herein provide easy to remove valves.

Figure 1:
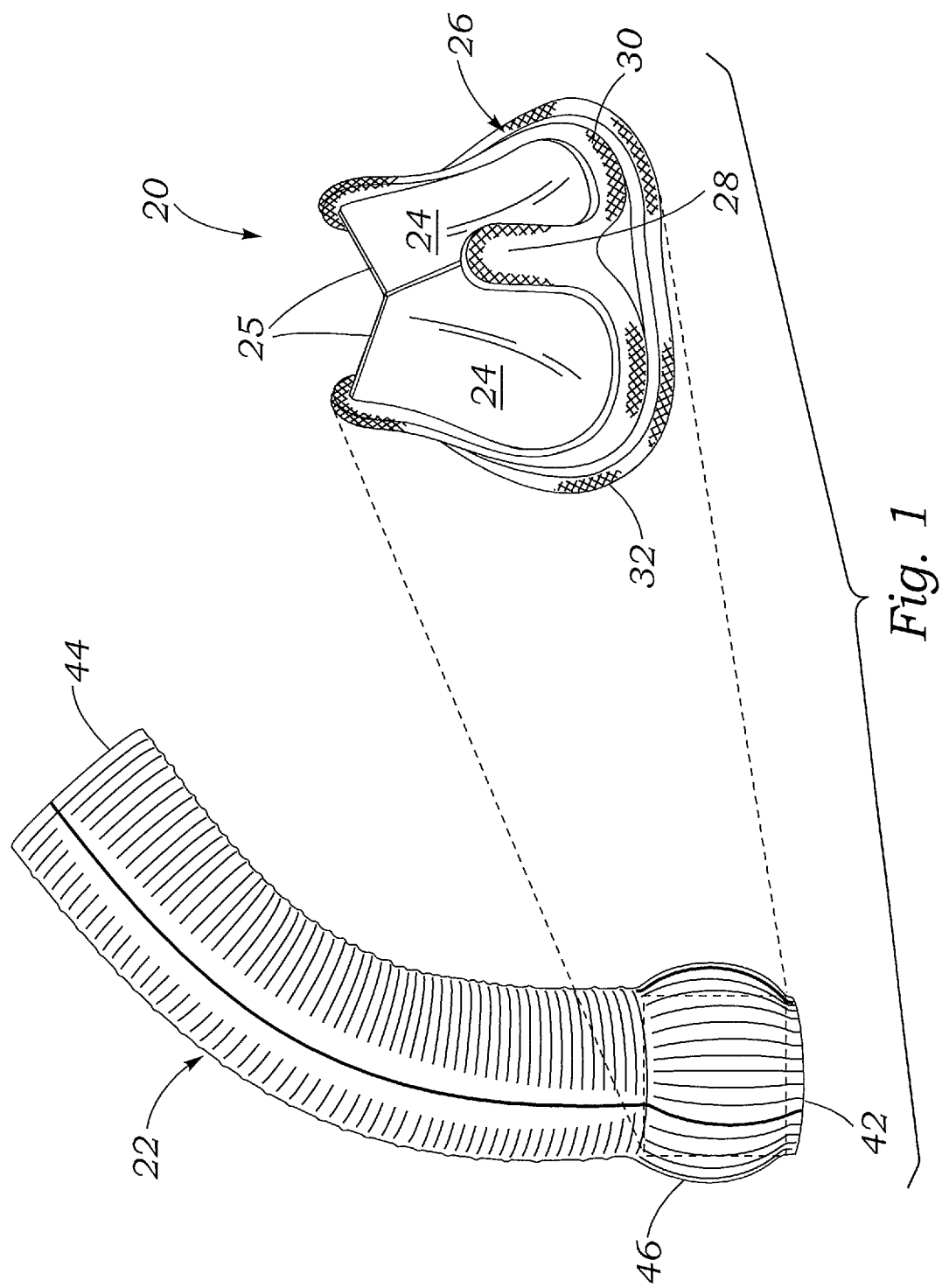
FIG. 1 is an exploded view of the combination of a bioprosthetic heart valve coupled to an aortic conduit graft of the present application to form a valved conduit.

FIG. 1 is an exploded view of an exemplary valved conduit VC comprising the combination of a bioprosthetic heart valve 20 coupled to an aortic conduit graft 22. As suggested schematically, the prosthetic heart valve 20 is positioned within one end of the conduit graft 22. Such a valved conduit VC may be used for replacing a native aortic valve and the ascending aorta. Of course, certain principles disclosed herein would also apply to replacement of the pulmonary valve and the pulmonary artery.

The heart valve 20 includes a rigid or semi-rigid stent supporting a plurality of flexible leaflets 24 (typically three) that are mounted to a peripheral stent structure 26 and form fluid occluding surfaces within the valve orifice to form a one-way valve. The stent structure 26 includes a plurality of generally axially extending commissures 28 circumferentially distributed around the valve between and in the same number as the number of leaflets 24. Although not shown, additional components of the heart valve 20 typically include an inner stent and/or wireform support structure that provide a structural skeleton surrounding an inflow orifice and extending up the commissures 28. The inner components of the heart valve 20 may be made of suitable metal or plastic. As is well known, adjacent flexible leaflets 24 connect to and extend upward to meet along each of the commissures 28. In the illustrated embodiment, the structural components of the heart valve 20 support each flexible leaflet 24 along a valve cusp 30 and along two commissure 28 edges. A free edge 25 of each leaflet 24 extends inward toward a central flow orifice and coapts, or mates, with the free edges of the other leaflets, as shown. The valve orifice is oriented around an axis along an inflow-outflow direction through the valve. The valve commissures 28 project in the outflow direction, with the convex valve cusps 30 extending in the inflow direction between adjacent commissures. A sewing ring 32 on the inflow end conforms to the undulating contours of the valve cusps, or defines a generally circular, planar ring. The present application should not be considered limited to a particular valve construction unless explicitly stated herein. Also, it will be understood that the sewing ring 32 may be conventional, that is unmodified from an existing heart valve sewing ring, or may be modified as described below.

The conduit graft 22 defines a generally tubular structure that extends from an inflow end 42 to an outflow end 44. In the embodiment shown, the valve 20 is associated with the conduit graft 22 in such a way that the valve leaflets 24 control flow of blood through the conduit by permitting blood flow into the conduit (e.g., blood flow into the aorta, when the conduit is used for aortic replacement) while preventing flow of blood out of the conduit in the opposite direction (i.e., back into the left ventricle of the patient when used for aortic replacement).

The illustrated conduit graft 22 is particularly suited for attachment within the aortic annulus and ascending aorta, and as such closely matches the aortic root anatomy and includes an enlarged region or bulge 46 close to the inflow end 42 that conforms to the sinuses of valsalva just above the aortic annulus. In the preferred embodiment, the conduit graft 22 comprises a tubular textile structure, such as Dacron, sealed with a bioresorbable medium such as gelatin or collagen. A majority of the conduit graft 22 includes a circumferentially corrugated (i.e., grooved) or pleated sidewall that provides longitudinal flexibility and radial compressibility while ensuring that the graft does not unduly radially expand under the pressure of blood flowing therethrough. The enlarged region or bulge 46 may be configured with longitudinal corrugations that are more radially expandable than the circumferential pleats to allow expansion at that location into the Valsalva sinuses. The conduit graft 22 desirably has a length of from a few centimeters to 10-12 centimeters.

In one embodiment, the conduit graft 22 may be a Vascutek® Gelweave Valsalva™ Grafts gelatin sealed, aortic root graft that is indicated for aortic root replacement using valve sparing or replacement techniques, and available from the Vascutek business of Terumo Cardiovascular Systems Corporation of Ann Arbor, Mich. As explained below, the use of a bioresorbable medium to provide a temporary seal to the implanted graft is preferred and may be preassembled with the exemplary bioprosthetic heart valves disclosed herein. However, the exemplary bioprosthetic heart valves may also be pre-assembled with other sealed grafts or conduits, such as those that utilize non-bioresorbable material. It should be understood that unless excluded by claim language, a variety of conduits are contemplated.

FIG. 2 shows the valved conduit VC coupled to a delivery handle 50, while FIG. 3 is an exploded view of the components. The delivery handle 50 includes an ergonomic grip 52 on a proximal end, and a shaft 54 extending distally and terminating in a valve holder 56. The valve holder 56 is shown schematically, and maybe any one of a variety of holder types. For example, the holder 56 may include three outwardly projecting arms which contact and are attached to tips of the commissures 28 of the heart valve 20.

The heart valve 20 is shown exploded and missing a fabric covering, with a stent and leaflet subassembly 60 above an exemplary enlarged and modified sewing ring 62. It should be noted that the lower end of the stent and leaflet subassembly 60 has a gently undulating configuration with three downwardly-bowed cusps 64 alternating with upward rises 65 at the location of the commissures 28. Likewise, the sewing ring 62 has an undulating configuration to match the lower end of the stent and leaflet subassembly 60, as will be described in more detail below.

An assembly process comprises attaching the valve holder 56 to the prosthetic heart valve 20 prior to attachment to the conduit graft 22. The grip 52 of the handle 50 is inserted from the inflow end (right side) of the conduit graft 22 and passed therethrough until the sewing ring 62 contacts the graft and the two are sewn together. The present application discloses a number of ways for coupling the prosthetic heart valve 20 to the conduit graft 22, and thus this assembly process may apply to any of the embodiments described herein.

FIG. 4 is an enlargement of the lower or inflow end of the valved conduit VC illustrating the exemplary sewing ring 62 minus an outer fabric covering. As also seen in isolation in FIG. 5, the sewing ring 62 comprises a generally annular waffle-like member of soft, suture-permeable material, such as silicone. As also seen in the radial cross-section of FIG. 4A the sewing ring 62 has a central, generally vertical wall 70, an outer flange 72, and an inner ledge 74. Both the outer flange 72 in the inner ledge 74 connect to a lower end of the central vertical wall 70 and project therefrom. The outer flange 72 extends outward at a slight upward angle, and connects to the vertical wall 70 via a series of circumferentially-oriented ribs 76, which define open cells 78 therebetween. The inner ledge 74 extends generally radially inward and has no such ribs.

With reference to FIG. 4A, internal components of the heart valve 20 are shown in sectional view. More specifically, the heart valve 20 includes an inner stent structure which in the illustrated embodiment includes two concentric bands 80, 82 that are enclosed in fabric 84 which is bunched or rolled into an outwardly-directed sewing tab 86. An outer edge of one of the leaflets 24 is sandwiched between the top of the stent structure and the bottom of a cloth-covered wireform 90. More specifically, the wireform 90 has a cloth covering with free ends that are folded together to form a sewing flap 92. Stitches (not shown) connect the sewing flap 92 to the sewing tab 86 below it.

The heart valve is positioned within the sewing ring 62, and the stent structure and sewing ring 62 are surrounded by an encompassing fabric cover 94. More specifically, the lower end of the stent structure including the two concentric bands 80, 82 abuts an outer end 96 of the inner ledge 74 of the sewing ring 62. The inner ledge 74 extends inward from the vertical wall 70 a sufficient distance such that the sewing tab 86 projects into the space therebetween. Conventional sewing rings do not have such a large inward ledge 74, and typically do not extend outward as far as the outer flange 72. The lower end of the conduit graft 22 attaches to the upper end 97 of the vertical wall 70 with stitches 98. Because of the space created between the heart valve 20 and the vertical wall 70, a surgeon can insert a scalpel therebetween to easily excise the heart valve if necessary, such as in a redo operation. That is, the radial extent of the inner ledge 74 creates the space between the heart valve and the sewing ring which facilitates the redo operation.

It should be noticed that the outer flange 72 of the sewing ring 62 travels in an undulating path which is more pronounced than the path circumscribed by the upper end 97 of the vertical wall 70. In a preferred embodiment, the conduit graft 22 is generally circular and planar on its lower end prior to attachment to the heart valve. Alternatively, as described below, the lower end of the conduit graft 22 may be cut so as to match the undulating shape of the upper end 97 of the vertical wall 70 of the sewing ring 62. Because the upper end 97 of the vertical wall 70 has a very gentle scalloped or undulating configuration, a minimum amount of wrinkling or puckering of the fabric of the conduit graft is seen when the lower end is attached to the vertical wall 70. On the other hand, the more pronounced undulation of the outer flange 72 better fits the undulating shape of the aortic annulus. That is, in use, the surgeon attaches the outer flange 72 of the sewing ring 62 to the aortic annulus using an array of pre-installed parachute sutures, as is well known in the art.

Figure 6A:
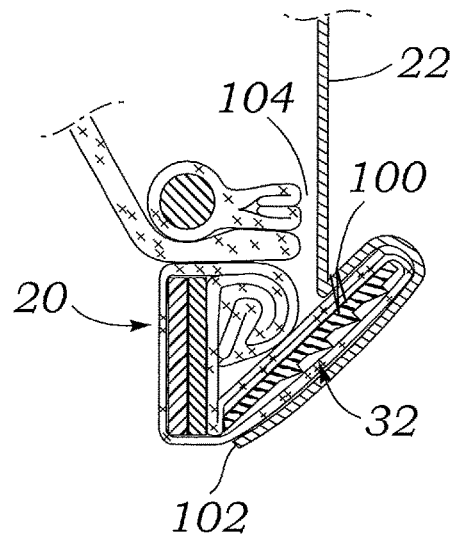
FIGS. 6A and 6B are radial sectional views through a lower end of a valved conduit showing alternative configurations of attachment between the conduit and valve.
Figure 6B:
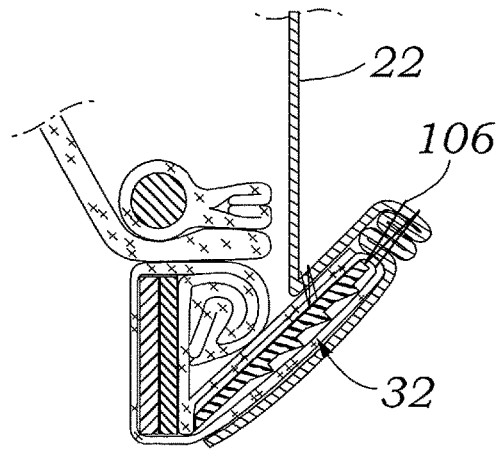

FIGS. 6A and 6B are radial sectional views through a lower end of a valved conduit VC showing alternative configurations of attachment between the conduit graft 22 and valve 20. The heart valve 20 is of conventional construction wherein the sewing ring 32 projects outward at an angle from a lower end of the stent structure. The sections illustrated in FIGS. 6A and 6B are taken through cusps of the heart valves.

In FIG. 6A, the conduit graft 22 extends downward to a line just inside the outer edge of the sewing ring 32, and is attached thereto using stitches 100. A length of the conduit graft 22 then wraps around the sewing ring 32 and terminates at a lower end 102. Although not shown, stitches are typically provided at spaced locations to maintain the conformal contact between the conduit graft and sewing ring, as shown. Again, a space 104 between the conduit graft 22 and the valve 20 facilitates cutting the conduit graft just above the heart valve for a redo operation. A similar configuration is shown in FIG. 6B, but a series of pleats or folds 106 are formed in the fabric of the conduit graft 22 at the outer edge of the sewing ring 32. This provides an extension of the sewing ring which helps during the implantation operation. That is, there is a greater amount of material through which to pass sutures, which reduces the chance of passing the needle through the delicate areas of the heart valve.

Figure 7:
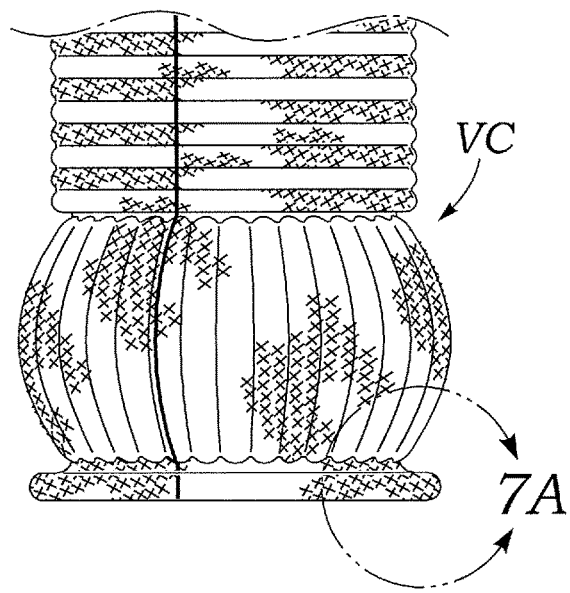
FIG. 7 is an elevational view of the inflow end of a valved conduit.
Figure 7A:
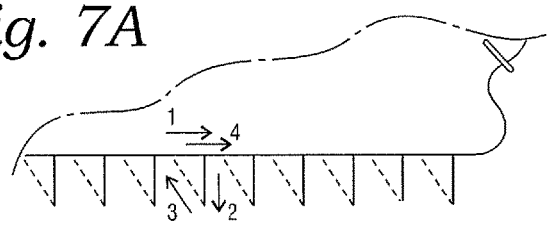
FIGS. 7A and 7B are schematic views of two different stitch patterns that can be used between the conduit and valve.
Figure 7B:
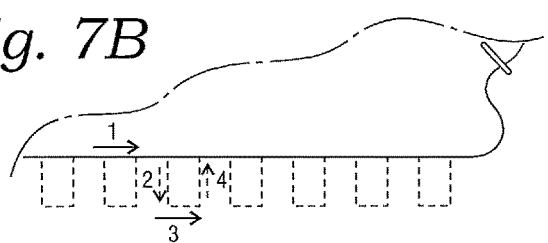

FIG. 7 again shows the inflow end of a valved conduit VC, and FIGS. 7A and 7B are schematic views of two different stitch patterns that can be used between the conduit graft and heart valve. In FIG. 7A, a backstitch technique is utilized which attaches the crease of the conduit smoothly and firmly to the sewing ring, leaving no gap that could cause leakage at the attachment site. The backstitch comprises sewing a first stitch (1) about 1 mm long circumferentially around the crease of the conduit, then sewing down (2) through the sewing ring and out of the covering cloth on the proximal side of the sewing ring. The needle is then inserted at (3) back into the sewing ring through the same hole of the cloth and exits ½ mm back from the previous stitch on the conduit. Stitch (4) is forward 1 mm. This pattern is then repeated around the entire circumference of the assembly. The use of this sewing technique is advantageous in that it avoids exposed sutures showing on the bottom of the sewing ring, and minimizes the "puckering" of the sewing ring cloth on the proximal end of the valve.

Alternatively, the embodiment in FIG. 7B uses an in-and-out stitch technique which improves assembly speed and requires fewer stitches to attach the conduit to the sewing ring. The process involves sewing one stitch (1) about 1.5 mm long circumferentially along the fold of the conduit, and then sewing down (2) through the sewing ring. A 1.5 mm stitch (3) is then placed under the stent cloth and passed through the sewing ring to exit (4) back on the fold of the conduit, repeating this pattern around the entire circumference of the assembly.

Figure 8:
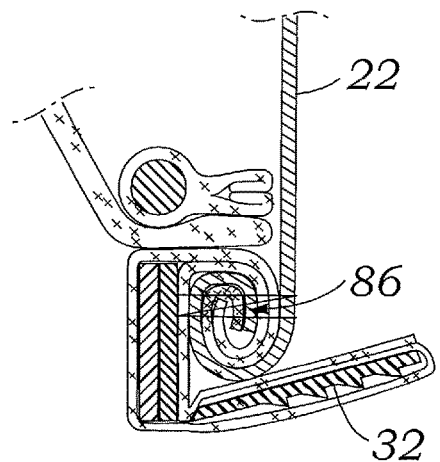
FIG. 8 is a radial sectional view through a lower end of a valved conduit wherein the bottom end of the conduit is wrapped and sewn together with a fabric tab of the heart valve.

FIG. 8 is conduit graft/valve connection in which a lower end of the conduit graft 22 is wrapped and sewn together with a rolled sewing tab 86 of the heart valve 20. This configuration requires assembly of the graft and valve together at the time of manufacture, whereas some of the embodiments described herein can utilize fully fabricated heart valves coupled to secondary structure.

Figure 9:
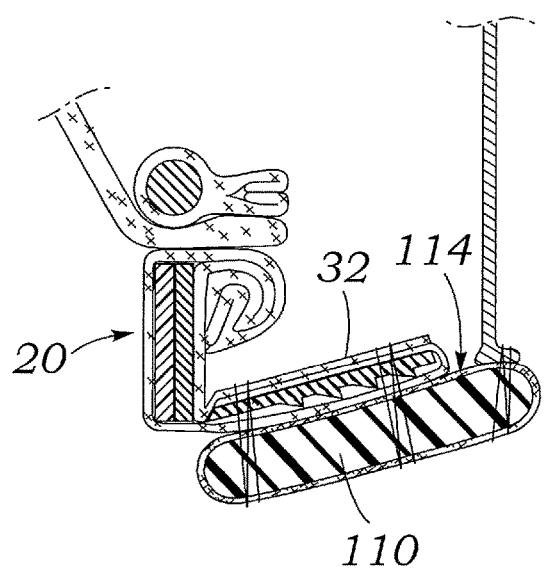
FIGS. 9-10 are radial sectional views through a lower end of the valved conduit wherein the conduit attaches to a secondary sewing ring which, in turn, attaches to a primary sewing ring of the heart valve.
Figure 10:
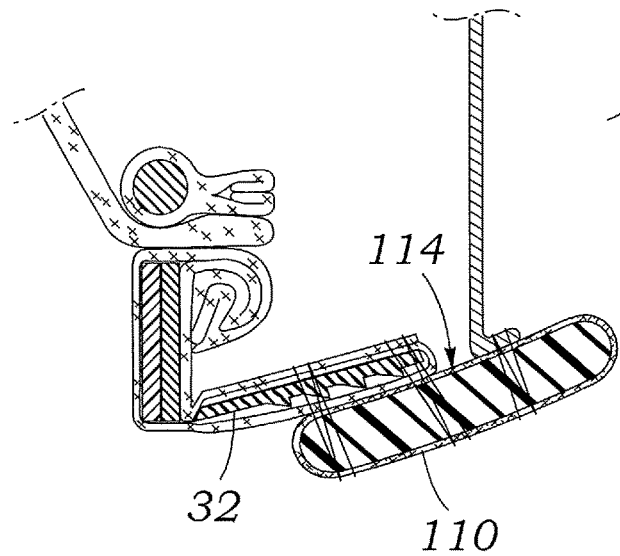

FIGS. 9-10 are radial sectional views through a lower end of the valved conduit wherein a secondary sewing ring 110 is utilized for connecting the conduit graft to the valve. The valve is conventional, with an outwardly angled sewing ring 32. In FIG. 9, the secondary sewing ring 110 attaches to the bottom side of the primary sewing ring 32 with, for example, stitches. The secondary sewing ring 110 extends the length of the primary sewing ring 32, but a portion projects outward and the lower end of the conduit graft 22 attaches thereto with stitches, for example. In FIG. 10, the secondary sewing ring 110 only overlaps about the outer half of the primary sewing ring 32, and a greater width extends outward to which the conduit graft 22 is attached. In each of the configurations shown in FIGS. 9-10, the secondary sewing 110 is used to provide a platform used to sew the assembly to the aortic annulus. Consequently, the redo operation is made relatively simple by severing the secondary sewing ring 110 just inside the conduit graft 22.

Figure 11:
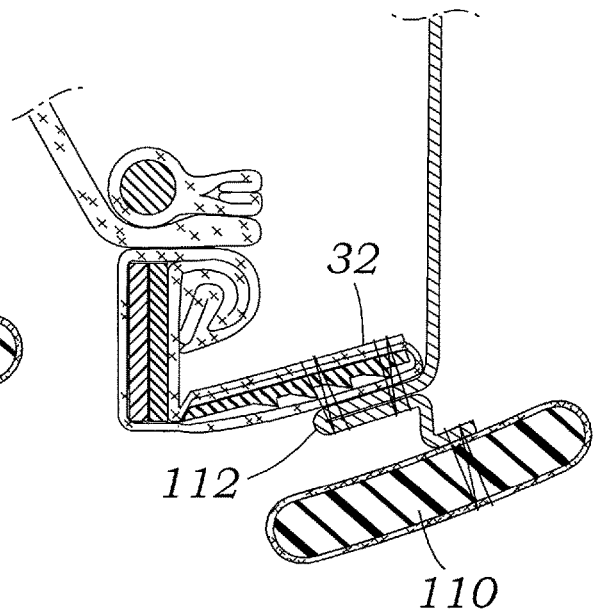
FIG. 11 is a radial sectional view through a lower end of the valved conduit wherein the conduit is folded and attaches to the heart valve sewing ring, and also to a secondary sewing ring.

FIG. 11 shows a secondary sewing ring 110 attached to the bottom end of the conduit graft 22, which, in turn, attaches to the lower side of the primary sewing ring 32. A fold 112 in the fabric of the conduit graft provides a flap to which the primary sewing ring 32 is sewn. In FIG. 11 the secondary sewing ring 110 is also used as a platform to sew to the aortic annulus, but the redo operation is accomplished by severing the primary sewing ring 32.

FIG. 12 illustrates a configuration where the valved conduit 22 attaches to a sewing band 120 which, in turn, attaches to a fabric sewing tab 86 of the heart valve 20. In this embodiment, the heart valve 20 includes no primary sewing ring. The sewing band 120 has a generally conical configuration with a protective cap 122 on an inner end. The protective cap 122 may be made of a number of different materials, preferably a polymer such as Delrin. Stitches 124 are used to connect the sewing band 120 to the sewing tab 86 of the heart valve 20, while the lower end of the conduit graft 22 is also sewn to a location on the sewing band which leaves a relatively large portion for use to sew the assembly to the aortic annulus. In a redo operation, the surgeon need only sever the stitches 124 connecting the sewing band 120 to the heart valve 20, and the protective cap 122 helps delineate and protect the inner end of the sewing band 120 from damage.

FIG. 13 shows the primary sewing ring 32 of a heart valve 20 attached to a secondary sewing ring 130 via a ring adapter 132 having cutting guides 134. FIG. 14 is a perspective view of the ring adapter 132 and schematically shows the path of sutures 136 used to secure the ring to the sewing ring. FIG. 14A is an enlarged view of one cutting guide 134 from the top of the ring adapter 132. The ring adapter 132 comprises a generally flat (or undulating if desired) disc-shaped annulus which conforms to the top side of the primary sewing ring 32. Adjacent sutures 136 are tied to each other above the surface of the ring adapter 132 at spaced locations 138 around the circumference. Each suture 136 extends clockwise or counterclockwise, passing down through one of a pair of anchor holes 140 and looping downward through the primary sewing ring 32 and through a portion of the secondary sewing ring 130, such as shown at 142 in FIG. 14. The sutures 136 then comes up through a second hole 144 and crosses over the cutting guide 134. The suture passes down through a third hole 146 and again loops through the primary sewing ring 32 and secondary sewing ring 130. Finally, the sutures 136 come up through another of the anchor holes 140 and ties to an adjacent suture. This arrangement permits the detachment of the heart valve from the secondary sewing ring 130, which is attached to the annulus and the conduit graft 22, by simply severing each of the separate sutures 136 at the cutting guides 134.

Figure 15:
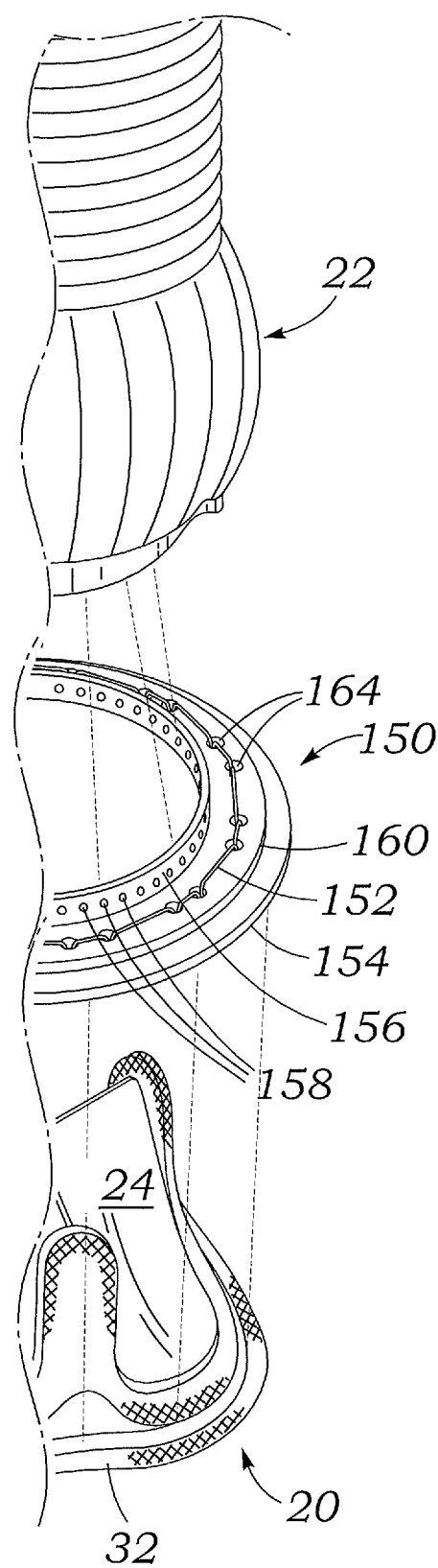
FIG. 15 is a partial exploded view of an alternative valved conduit assembly wherein an adapter ring is used between the conduit and heart valve.
Figure 15A:
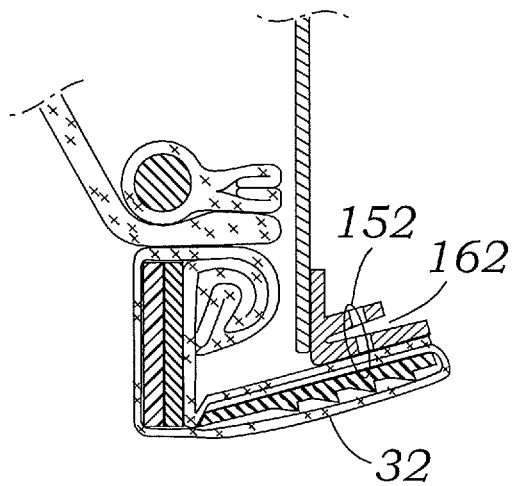
FIG. 15A is a radial sectional view through a lower end of the valved conduit showing the position of the adapter ring and how it attaches to the conduit and valve.

FIG. 15 is a partial exploded view of an alternative valved conduit assembly wherein an adapter ring 150 is interposed between the conduit graft 22 and heart valve 22. As seen in FIG. 15A, the adapter ring 150 is positioned on the upper or outflow side of the heart valve sewing ring 32 and attaches thereto with a line of stitches 152. The adapter ring 150 includes a lower flange 154 that conforms to the top of the sewing ring 32 (flat or undulating). An inner, generally axially-oriented flange 156 projects upward and the bottom end of the conduit graft 22 connects thereto, such as with stitches through a line of suture holes 158 (FIG. 15). The adapter ring 150 also includes an intermediate flange 160 which generally projects outward parallel to the lower flange 154 such a circumferential somewhat V-shaped gap 162 is formed therebetween. The line of stitches 152 crosses the gap 162 and through holes 164 in the intermediate flange such that a surgeon can disconnect the heart valve 20 from the conduit graft 22 and adapter ring 150 by passing a scalpel into the gap. The adapter ring 150 may be made of a suitable rigid polymer, such as Delrin or nylon, so that the scalpel does not easily pass through it.

Figure 16A:
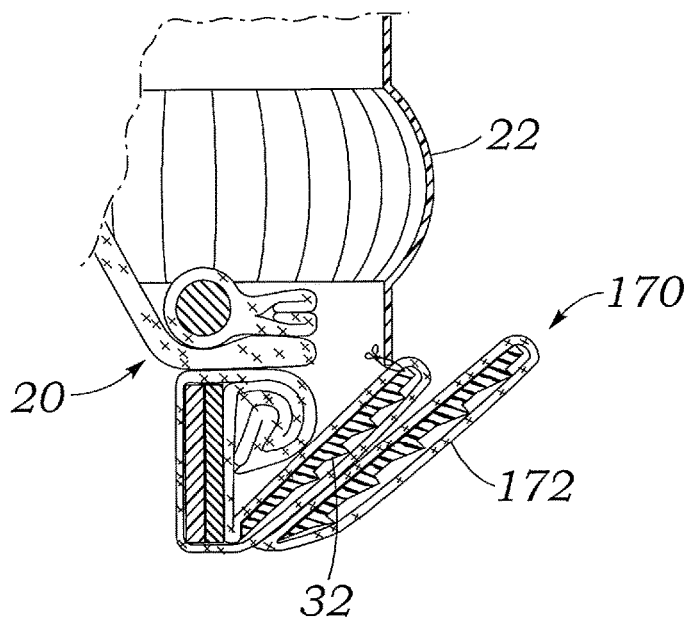
FIGS. 16A-16C are radial sectional views through a lower end of a valved conduit wherein the heart valve has a dual sewing ring and the lower end of the conduit attaches to different locations thereon.
Figure 16B:
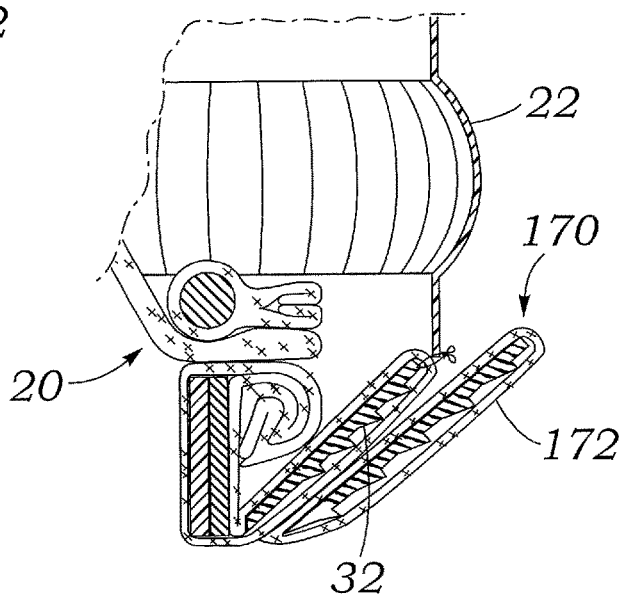
Figure 16C:
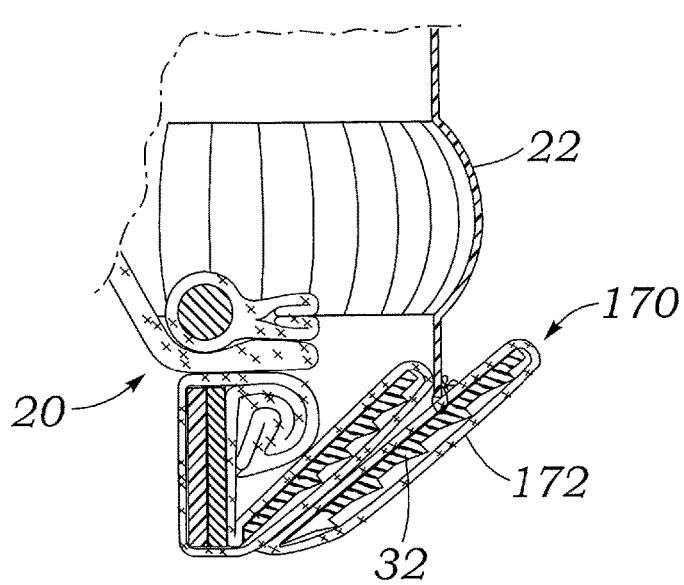

FIGS. 16A-16C are radial sectional views through a lower end of a valved conduit wherein the heart valve 20 has a dual sewing ring 170 formed by a primary sewing ring 32 and a secondary sewing ring 172 attached outward therefrom. The lower end of the conduit graft 22 connects to the primary sewing ring 32 at its upper side (FIG. 16A), to its outer end (FIG. 16B), or to its lower side (FIG. 16C). In each case, the secondary sewing ring 172 provides a relatively large platform which the surgeon can use to sew the assembly to the surrounding aortic annulus.

Figure 17:
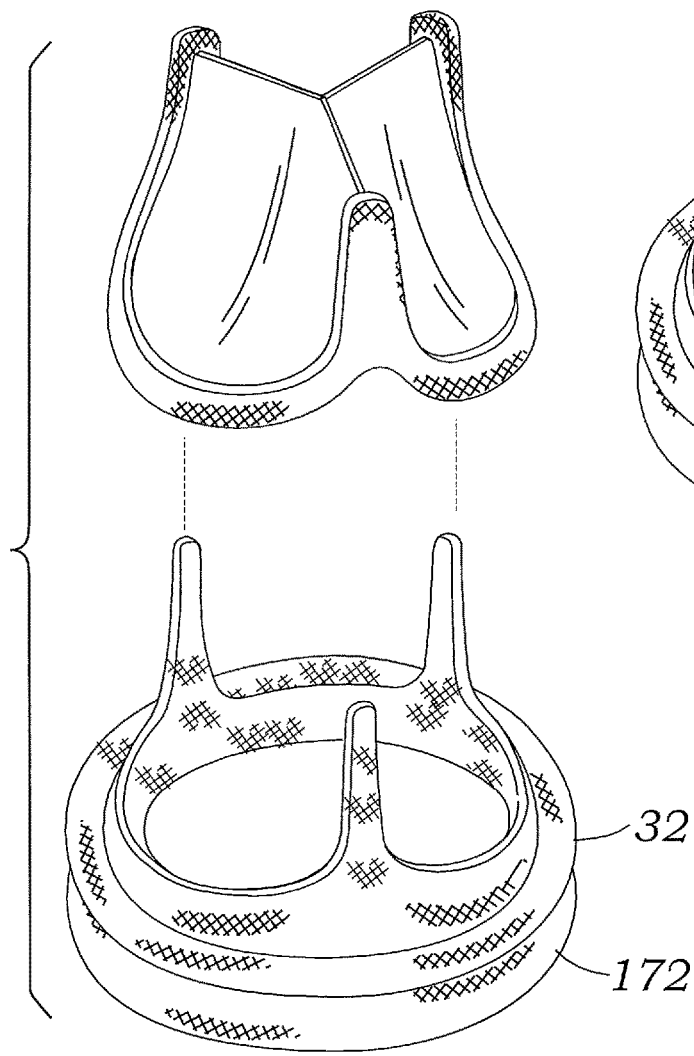
FIG. 17 is an exploded view of a heart valve having a dual sewing ring.
Figure 17A:
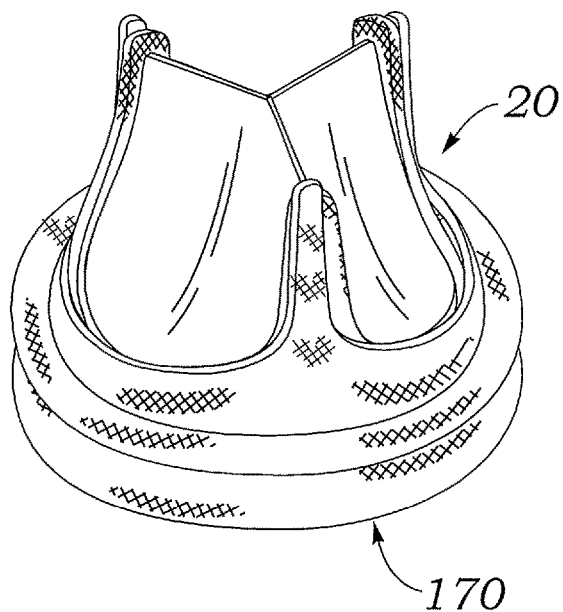
FIG. 17A is an assembled view of the heart valve.

FIG. 17 is an exploded view of a heart valve having the dual sewing ring 170, and FIG. 17A is an assembled view of the heart valve 20. Both the primary sewing ring 32 and the secondary sewing ring 172 are generally flat conical pieces of suture-permeable material, such as silicone, covered with cloth. As seen in the section views of FIGS. 16A-16C, both sewing ring 32, 172 attached around substantially thin seam lines so that they can easily pivot with respect to one another, and with respect to the rest of the heart valve. In particular, the secondary sewing ring 172 can be pivoted outward so the surgeon can easily pass sutures through it during implantation.

FIG. 18A is a longitudinal sectional view through a lower end of a conduit graft 22 having a tubular hem 180 formed on a lower end enclosing a locking ring 182. For example, FIG. 18B shows a C-shaped locking ring 182 having a hollow throughbore within which a drawstring 184 may be placed. FIG. 18C is a sectional view in which the locking ring 182 at the bottom end of the conduit graft 22 is held within an outwardly opening channel 190 of the ring member 192 secured to a heart valve 20. For example, the ring member 192 may be metallic and may be welded to an outer metal band 82 of the heart valve, or the ring member 192 may be connected with sutures, adhesive, or other such solutions. The conduit graft 22 couples to the heart valve 20 by interference between the locking ring 182 and the channel 190. In particular, the C-shaped ring 182 may have a relaxed shape with a larger diameter than the diameter of the channel 190, wherein tensioning the drawstring 184 after positioning the lower end of the conduit graft 22 outside of the ring member 192 constricts the ring 182, thus causing it to engage the channel 190. Alternatively, the C-shaped locking ring 182 may have a relaxed diameter that is approximately the same as the channel 190, and may be flexed apart to allow it to pass over the valve structure and enter the channel 190 from its elastic recoil. The locking ring 182 desirably has an undulating shape as shown to match the undulating shape of the channel 190 that follows the ring member 192, or the two mating components may be circular/planar. In a valve redo operation, the surgeon need only disengage the locking ring 182 from the channel 190, and remove the valve. The C-shaped ring 182 is made of a metal or high-density plastic flexible enough to be compressed to a tighter radius, such as when tension is applied to the drawstring 184.

Figure 19A:
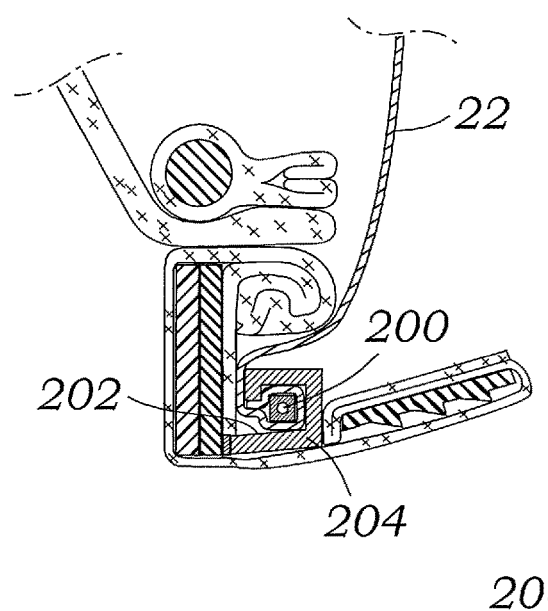
Figure 19B:
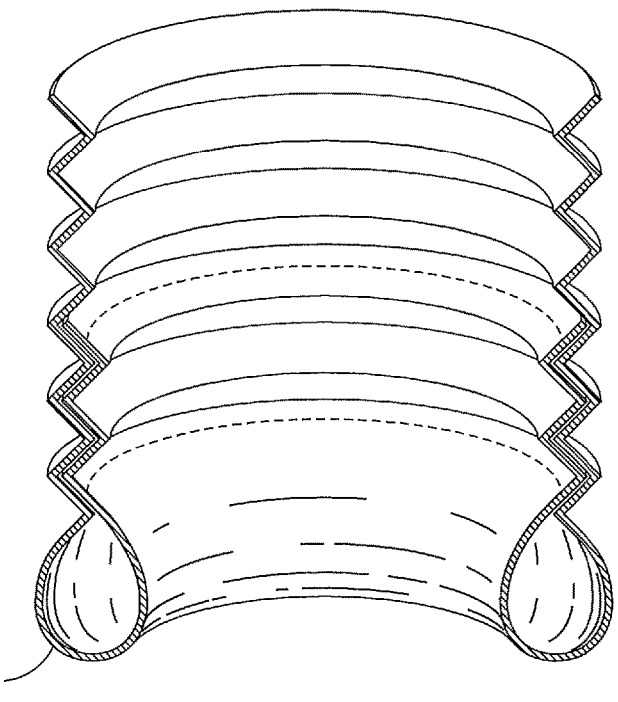
FIG. 19B is a longitudinal sectional view through a lower end of the conduit illustrating the tubular hem.

FIG. 19A illustrates a locking ring 200 hemmed to the lower end of a conduit graft 22 and secured within an inwardly opening locking channel 202 of a valve ring 204 secured to the heart valve 20. In this embodiment, it is the outward force of the locking ring 200 that couples the two parts together. FIG. 19B shows the lower end of the conduit graft 22 illustrating the tubular hem 206. The locking ring 200 is either discontinuous (e.g., C-shaped) and threaded through an opening in the tubular hem 206, or maybe continuous and enclosed when the hem is formed.

Figure 20A:
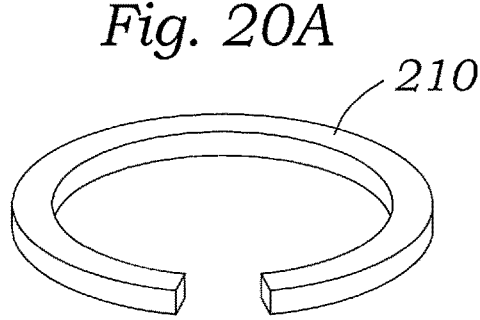
FIGS. 20A-20D illustrate variations of locking rings for use with the configuration shown in FIG. 19A.
Figure 20C:
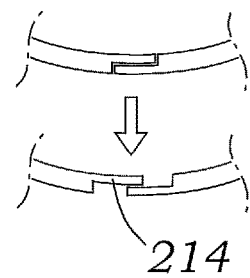
Figure 20B:
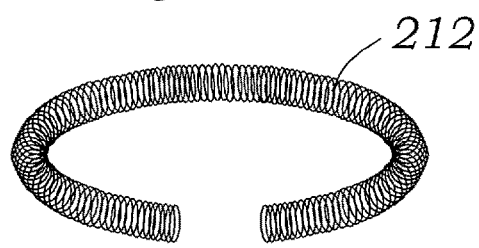
Figure 20D:
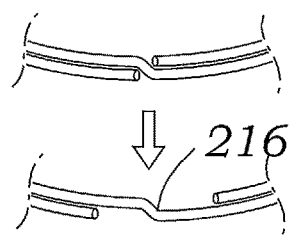

FIGS. 20A-20D illustrate variations of locking rings 200 for use with the configuration shown in FIG. 19A. For example, a simple C-shaped ring 210 in FIG. 20A may be squeezed to reduce its diameter and allow its passage into the channel 202 of the valve ring 204. FIG. 20B illustrates a coil spring-type locking ring 212 which is relatively flexible and easily passes into the channel 202, but has sufficient resiliency to retain the conduit graft 22 together with the heart valve 20. FIG. 20C illustrates a discontinuous locking ring 214 with overlapping features designed to slide over each other under compression or expansion. The progression shows the shape of the ring 214 from when it is compressed (above) to its relaxed shape (below) with a larger diameter which locks in the channel 202. Likewise, FIG. 20D illustrate another locking ring 216 with overlapping features that somewhat resembles a keyring. Again, the illustration on the top is compressed for entry into the channel 202, while the figure on the bottom shows the ring 216 expanded. The continuous locking rings are preferred because they do not form structural gaps at the lower end of the conduit graft which might permit paravalvular leakage.

Figure 21A:
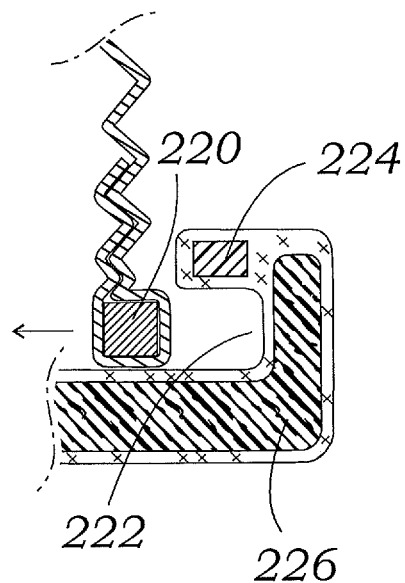
FIGS. 21A and 21B show a locking ring at the bottom of a conduit mating with an alternative inwardly-facing channel of an exemplary heart valve.
Figure 21B:
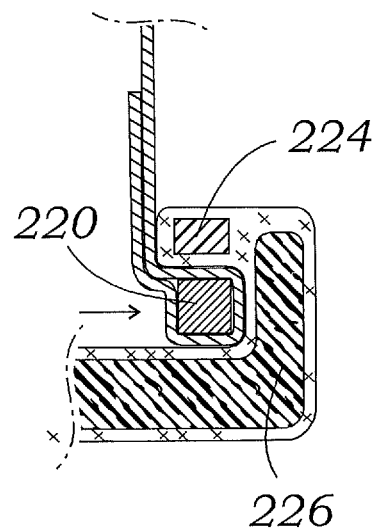

FIGS. 21A and 21B show a locking ring 220 at the bottom of a conduit graft 22 mating with an alternative inwardly-facing channel 222 of an exemplary heart valve. Instead of a solid ring forming a channel, the channel 222 is formed by a rigid ring 224 embedded within the sewing ring 226 of the valve. The locking ring 220 at the bottom of the conduit graft is compressed, as seen in FIG. 21A, so that it can fit within the channel 222, and then released so that it expands outward to its relaxed shape into the channel, as seen in FIG. 21B.

Figure 22:
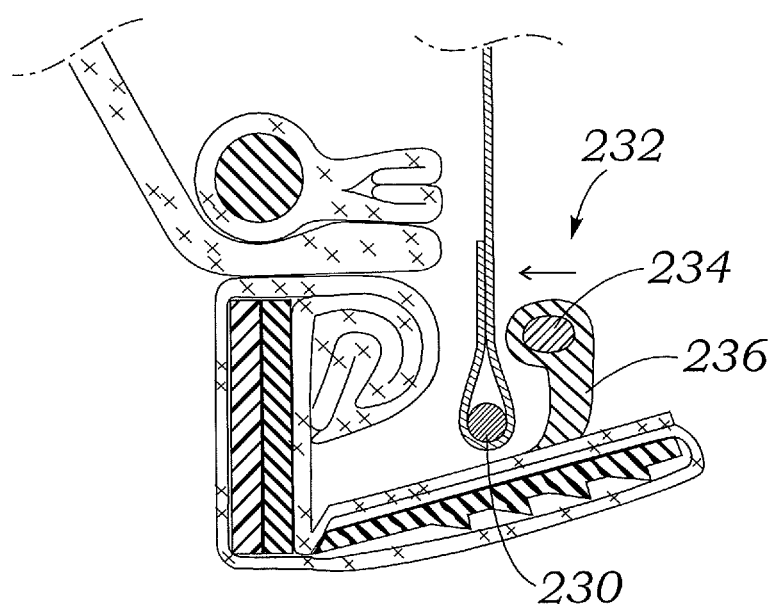
FIG. 22 is a radial sectional view through a lower end of a valved conduit showing a locking ring hemmed to the lower end of the conduit and an adjustable clamp provided on the heart valve.

FIG. 22 illustrates a still further embodiment wherein a circular locking ring 230 hemmed to the lower end of the conduit graft 22 is captured by an adjustable clamp 232 provided on the heart valve 20. For example, the adjustable clamp 232 may comprise a drawstring 234 captured within a tubular hem of a piece of fabric 236 connected to the valve sewing ring 32. Alternatively, the element 234 contained within the hemmed fabric 236 may be a discontinuous ring or spring member which can be expanded to allow entry of the locking ring, 230 then released to constrict inward, thus capturing the locking ring and conduit graft 22. Again, in a reverse procedure, the surgeon can expand the adjustable clamp 232 and remove the valve from the conduit graft in a redo operation.

Figure 23A:
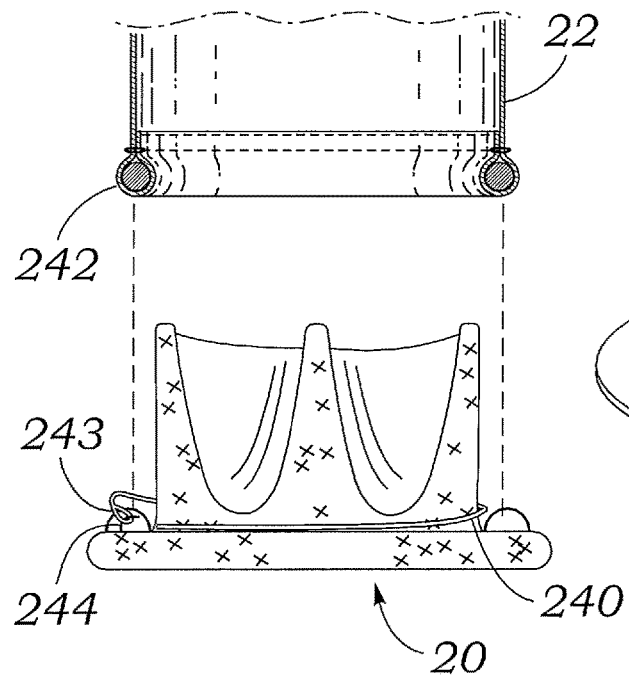
FIGS. 23A and 23B are exploded and assembled views, respectively, of an alternative connection arrangement between a conduit graft and a prosthetic heart valve utilizing a wire coil that passes through a hem of the conduit graft.
Figure 23B:
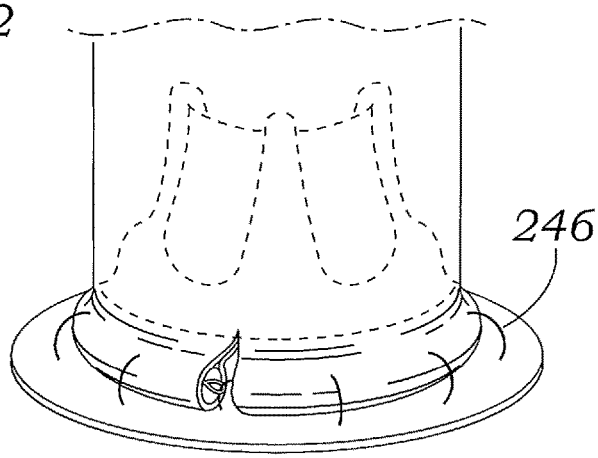

FIGS. 23A and 23B are exploded and assembled views, respectively, of an alternative connection arrangement between a conduit graft 22 and a prosthetic heart valve 20. A wire coil 240 anchors at one end to an upper side of the sewing ring 32 of the heart valve, and then passes through an opening in and around a hem 242 of the conduit graft. As seen in FIG. 23B, a loop 243 on the free end of the wire coil 240 catches on a small hook 244 or other such anchor also attached to the sewing ring 32. A number of spaced sutures 246 are provided to hold down the lower end of the graft 22 having the coil 240 therein.

Figure 24A:
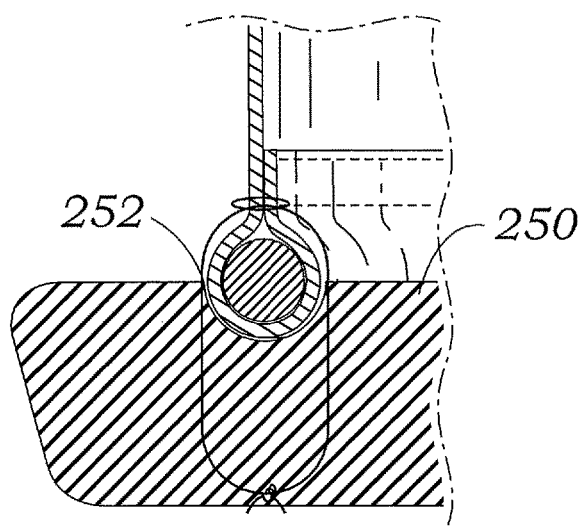
FIGS. 24A and 24B are alternative configurations of a sewing ring for use with the connection arrangement of FIGS. 23A and 23B.
Figure 24B:
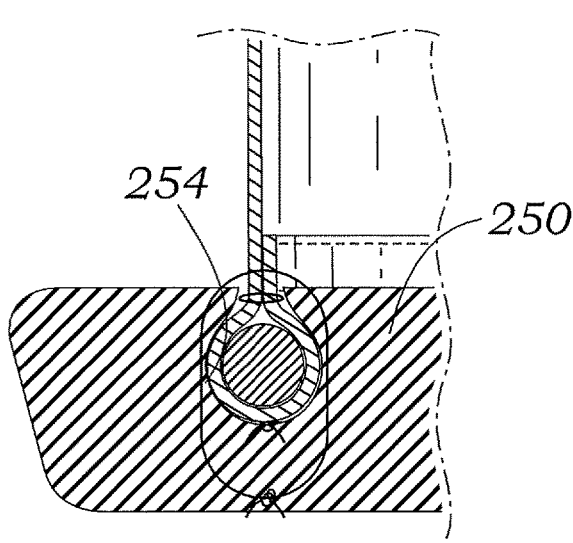

Grooves or other such depressions in the upper surface of the sewing ring 32 may be provided to help capture the lower end of the graft 22. For instance, FIGS. 24A and 24B show alternative configurations of a sewing ring 250, the former of which provides a shallow groove 252 and the latter of which provides a deeper pocket 254. The sutures 246 looped around the coil 240 can be tensioned to pull the lower end of the graft into the groove 252 or pocket 254, which helps prevent leakage between the two.

FIG. 25 illustrates a prosthetic heart valve 20 with a pair of coupling rings 260, 262 that attach thereto. More particularly, a lower coupling ring 260 includes a central aperture 264 larger than the commissure and leaflet structure such that the ring rests on the sewing ring 32. Likewise, the upper coupling ring 262 has a similarly-sized central opening 265 and sits on top of the lower coupling ring 260. The lower ring 260 has three recesses 266 evenly distributed on its upper surface and opening to the central aperture 264. The recesses 266 are generally shallow, arcuate, and flat, and feature a small bump 268 projecting upward in the middle. The upper coupling ring 262 includes three equidistantly spaced notches 270 that open inward to the central opening 265. The notches 270 register over the recesses 266 on the lower ring 260. Both of the coupling rings 260, 262 include a plurality of suture holes distributed around their peripheries to permit attachment to the sewing ring 32.

FIG. 26 shows the prosthetic heart valve 20 with the two coupling rings 260, 262 attached thereto. A conduit graft 22 exploded above the valve has a locking ring 272 attached to a lower end thereof. The locking ring 272 features three outwardly projecting tabs 274 that are sized to register with the notches 270 in the upper coupling ring 262. That is, the conduit graft 22 attaches to the heart valve 20 by engaging the locking ring 272 with the coupling rings 260, 262.

FIGS. 26A and 26B are plan and sectional views illustrating the engagement between the locking ring 270 and the coupling rings 260, 262. Each of the tabs 274 extends downward through a corresponding notch 270 in the upper coupling ring 262 and into one of the recesses 266 in the lower coupling ring 260. Rotating the assembly of the conduit graft 22 and locking ring 270 causes each of the tabs to rotate within the corresponding recess 266, eventually camming over the small bump 268 so as to be captured therein. For a redo operation, the procedure is reversed with the conduit graft 20 and locking ring 270 being rotated in the opposite direction to overcome the resistance of the bumps 268 and permit the tabs 274 to exit from the notches 270.

Figure 27A:
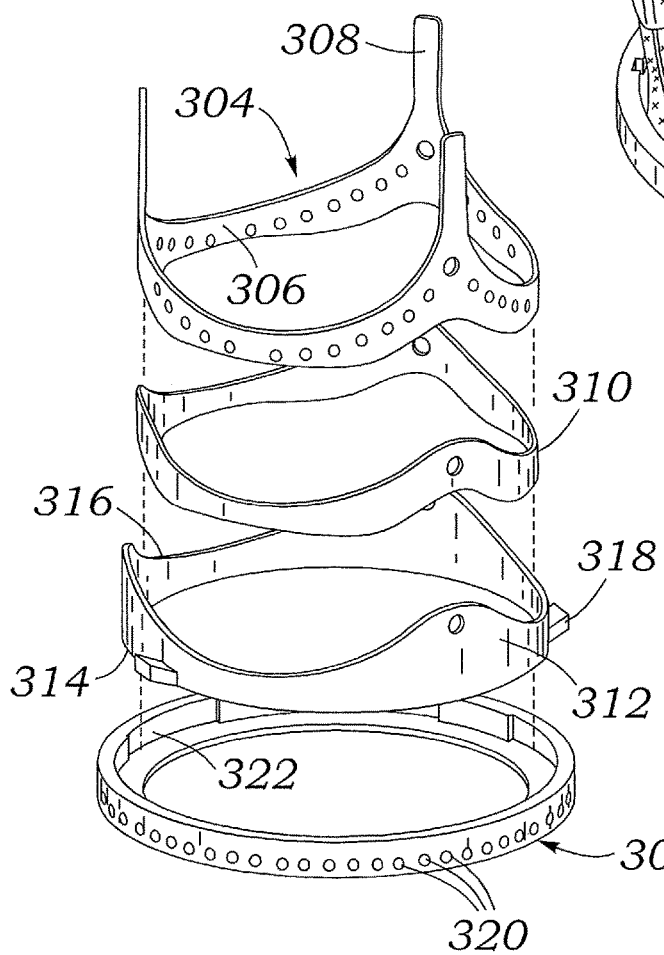
FIGS. 27A-27C are perspective and sectional views of an alternative prosthetic heart valve having a connection arrangement utilizing locking tabs on the heart valve that mate with channels in a sewing ring cuff.
Figure 27B:
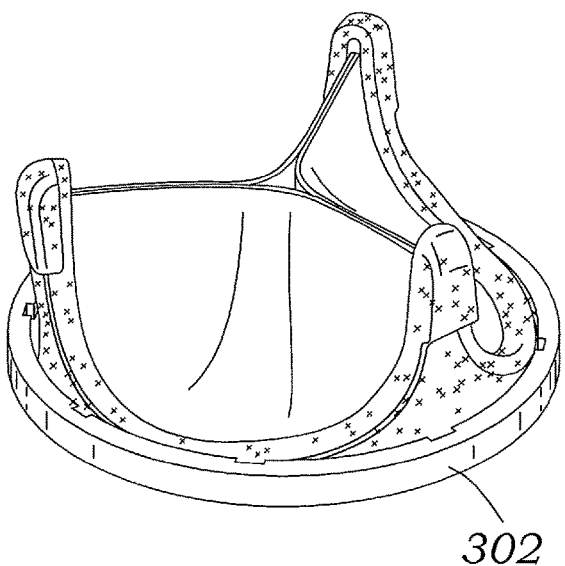
Figure 27C:
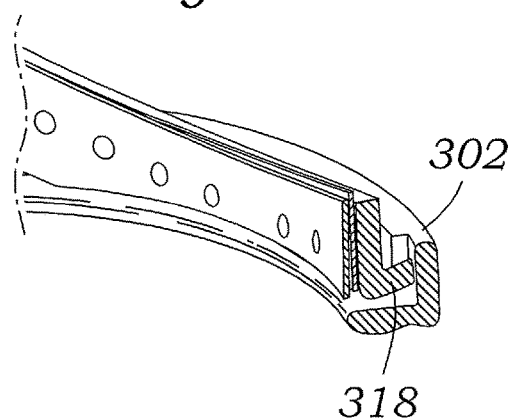

FIGS. 27A-27C illustrates an alternative connection arrangement wherein outward locking tabs on a prosthetic heart valve 20 mate with inwardly-facing channels in a sewing ring cuff 302. In general, the sewing ring cuff 302 contains a number of "female" bayonet mounting tracks and slots on its inner face while a ring connected to the heart valve 20 features an equal number of "male" barb protrusions which lock into the bayonet track. The conduit graft 22 attaches to the sewing ring cuff 302.

FIG. 27A shows some of the inner structural components of the heart valve 20, including an inner polymer stent 304 having an undulating band portion 306 with upwardly-projecting commissure posts 308. A metallic band 310 concentrically surrounds the stent 304 and also has an undulating shape, matching the undulating band portion 306. The stent 304 and band 310 are normally included in the prosthetic heart valve 20. A third locking band 312 concentrically surrounds the metallic band 310. The locking band 312 has a relatively planar lower edge 314 and undulating upper edge 316 that tracks the undulating shape of the metallic band 310. A number of angled barbs 318 project outward from the locking band 312. As seen in the sectional view of FIG. 29B, the barbs 318 project outward from the structure of the valve 20. The valve may include the stent 304, band 310, and locking band 312, or the barbs 318 may be incorporated into the metallic band 310, such as shown in the cross-section of FIG. 29B.

The sewing ring cuff 302 has a series of suture holes 320 on its exterior as well as a series of bayonet locking channels 322 that matched the barbs 318. Preferably, there are three barbs 318 and three bayonet locking channels 322. FIGS. 27B and 27C show engagement between the heart valve 20 and its outwardly projecting barbs 318 and the sewing ring cuff 302.

FIG. 28 illustrates the sewing ring cuff 302 above an outer anchoring member 330 that forms a part of the lower end of a conduit graft. The anchoring member 330 has a planar upper edge 332 and an undulating lower edge 334 with a plurality of suture holes therethrough. With reference to the cross-section of FIGS. 29A and 29B, the anchoring member 330 connects to both an outwardly extending sewing ring 336 via a fabric enclosure 338, and to the conduit graft 22 using sutures. The sewing ring 336 is used to attach the valve conduit to the aortic annulus 340. At the same time, the sewing ring cuff 302 attaches to the inner face of the anchoring member 330 using sutures, as seen in FIG. 29A. Finally, the prosthetic heart valve 20 engages the sewing ring cuff 302 using the barbs 318 and bayonet locking channels 322. Preferably, small mating ramps within the locking channels 322 retain the barbs 318 therein. As the barbs 318 flex past the ramps, they snap into place.

Desirably, when the barbs 318 snap into the docking area of the locking channels 322 they retain a slight downward deformation and thus exert a force between the sewing cuff and the valve body, thereby limiting relative motion and ensuring a good seal between two. The barbs 318 and respective channels 322 may be distributed non-uniformly in the circumferential direction such that the valve and sewing cuff are "keyed" thereby eliminating the possibility of positioning the valve incorrectly once the sewing ring cuff 302 has been implanted.

In practice, the sewing ring 336 and conduit graft 22 assembly could be sewn to the heart valve without the valve docked in place. This would allow the surgeon to have good visibility through the conduit into the ventricle during suturing of the sewing ring 336 to the annulus. Alternatively, the valve may be engaged with the sewing ring cuff 302 and then the entire assembly attached to the annulus/aorta. The prosthetic heart valve 20 can thus be easily engaged and disengaged from the sewing ring cuff 302, which remains attached to the anchoring member 330 and conduit graft 22, both of which are attached to the aortic annulus. Replacement of the valve in a redo operation would entail creating an aortotomy in the conduit graft 22, unlocking the valve 20, and then locking a new one in its place. Because the valve can easily be separated from and reattached to the sewing ring cuff 302, the valve can be supplied in glutaraldehyde and rinsed at the time of use, or supplied in dry format.

Figure 30:
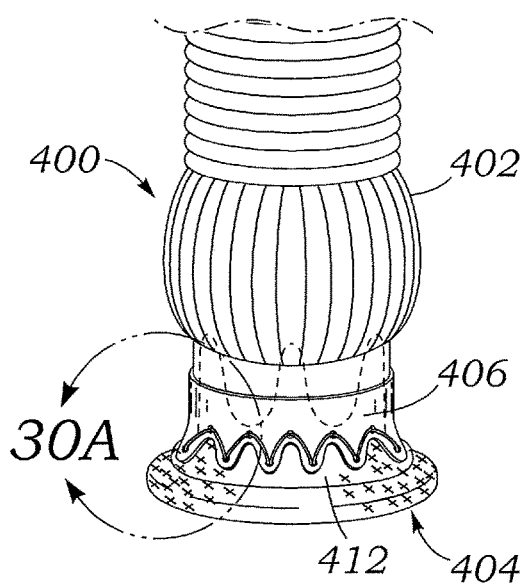
Figure 30A:
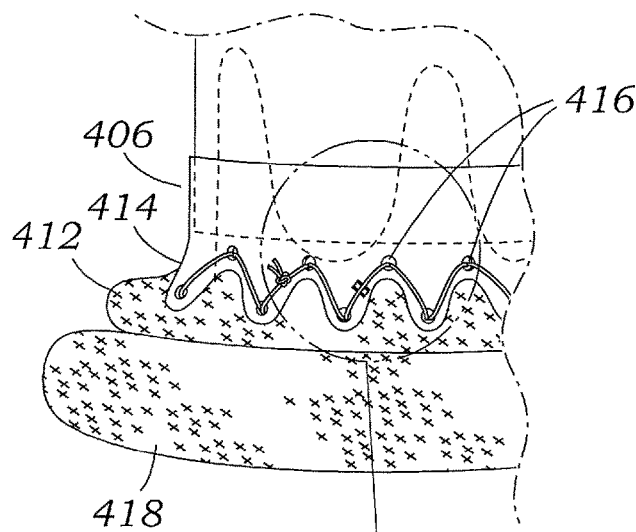
FIG. 30A is a close-up of a portion of the assembly.
Figure 31A:
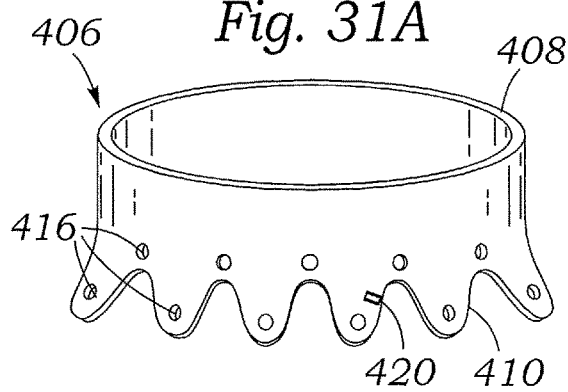
FIG. 31A is a perspective view of the intermediate band from the assembly of FIG. 30.

FIG. 30 is a perspective view of a still further valved conduit 400 wherein a conduit graft 402 and a prosthetic heart valve 404 are connected utilizing an intermediate ring or band 406. In this configuration, the conduit 402 is not directly attached to the valve 404. The generally tubular band 406 is seen by itself in FIG. 31A, and includes a circular upper edge 408 and a crenelated or crowned lower edge 410. The band 406 is desirably made of the same or similar material as the conduit graft 402 (stiff fabric or a rigid or semi-rigid plastic material) and pre-attached thereto by means of ultrasonic or vibration welding techniques. The lower edge of the conduit graft 402 can be placed internally, externally, or flush to the upper edge 408 and secured with welding, as mentioned, or with sutures as described below. A weld forms a robust hemostatic seal between the conduit graft 402 and band 406.

The subassembly of the conduit graft 402 and band 406 can then be attached to a sewing cuff 412 (or sewing ring) of the prosthetic heart valve 404 by means of attachment sutures 414 passed back and forth through a plurality of holes 416 in the band 406. The valve 404 may have a single or double sewing cuff 412, as described earlier. The holes 416 act as a template indicating where to pass the sutures 414, and are desirably distributed in a zig-zag pattern to enable the sutures to alternately pass through the conduit graft 402 and then the valve sewing cuff 412. The prongs of the crown-shaped lower edge 410 enable the band 406 to expand around various sized sewing cuffs 412. Once assembled, the completed valved conduit 400 can then be attached to the aortic annulus by passing implant sutures through an outer sewing cuff 418 (the illustrated embodiment includes a double sewing cuff, though a single sewing cuff may be used as well).

Figure 30B:
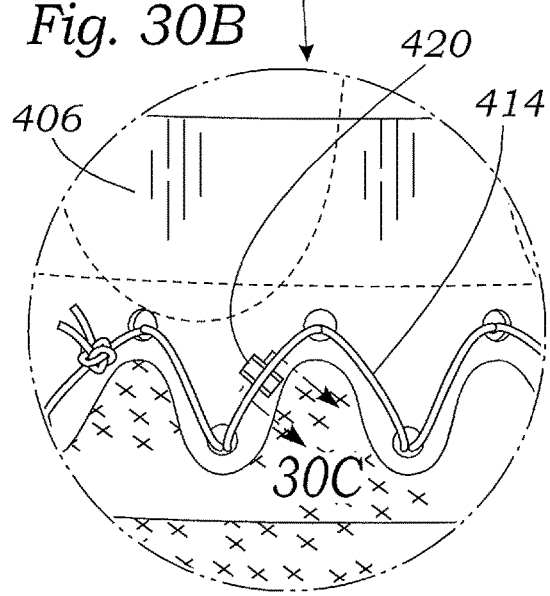
FIG. 30B is an enlargement of one edge of the intermediate band taken from FIG. 30A.
Figure 30C:
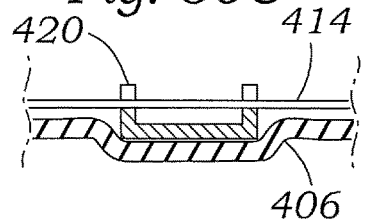
FIG. 30C is a section view through a cutting well thereon.

As seen best in FIGS. 30B and 30C, the band 406 features at least one cutting well 420 secured to its outer surface between two of the holes 416. The cutting well 420 comprises a small plastic channel across which the suture 414 passes. Although not shown, a small notch on both sides of the channel may be provided to hold the suture 414 in place perpendicularly spanning the channel.

If the prosthetic heart valve 404 needs to be replaced for a redo surgery, it can be easily removed from the band 406 by inserting a scalpel into the cutting well 420 thereof and cutting the suture 410 to remove it. More than one cutting well 420 may be provided. This will free the valve 404 from the band 406. The suture 410 is not tied to the band 406 so it can be removed with its loose ends simply pulling free from the band 406. The implant sutures connecting the valve sewing cuff 418 to the annulus can then be removed utilizing a scalpel, thus freeing the valve 404 from the annulus. A new valve can then be attached by passing sutures through the holes 416 on the band 406, through the sewing cuff 412, and then implant sutures through the outer cuff 418 and annulus.

For better visibility, the holes 416 may be ringed with colored ink or fabric, or grommets may be used for tactile feedback.

Figure 31B:
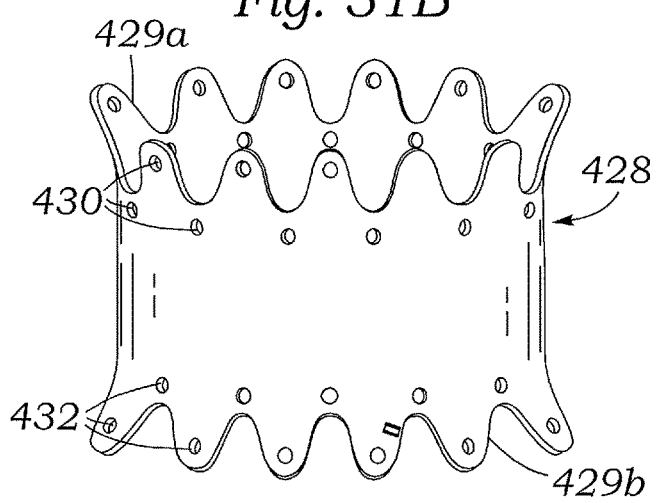
FIG. 31B is an alternative band having crown-shaped upper and lower edges.

FIG. 31B illustrates an alternative intermediate band 428 for connecting the conduit graft 402 and the prosthetic heart valve 404 that has crown-shaped upper and lower edges, 429a, 429b in a so-called "double crown ring." Again, the conduit 402 is not directly attached to the valve 404, and the intermediate band 428 works with a valve 404 that has a single or double sewing cuff or sewing ring. The band 428 attaches to the conduit graft 402 initially by means of suturing techniques using a series of holes 430 in a zig-zag pattern on the upper edge 429a of the double crown band 428. The conduit graft 402 is desirably placed internally to the double crown band 428. The double crown band 428 can be made of a stiff fabric or a rigid or semi-rigid plastic material. The band-to-conduit connection forms a robust hemostatic seal, which may be enhanced with a layer of silicone or other sealant therebetween. The subassembly of the conduit graft 402 and double crown band 428 can then be attached to the valve 404 by means of suturing thread utilizing a series of holes 432 in a zig-zag pattern on the lower edge 429b of the double crown band 428. The complete valved conduit is again attached to the aortic annulus by passing implant sutures through the single sewing cuff or an outer sewing cuff if the valve assembly has a double sewing cuff.

As before, if the valve 404 needs to be replaced for a redo surgery, it can be easily removed from the double crown band 428 by inserting a scalpel into a cut well 438 and cutting the suture to remove it. This will free the valve 404 from the double crown band 428, and the implant sutures attaching the valve 404 to the annulus can be removed from the sewing cuff utilizing a scalpel, freeing the valve completely. A new valve can then be attached by passing sutures through the holes 434 on the lower edge 436 of the double crown band 428, then through the sewing cuff, and then implant sutures through the outer cuff and annulus.

FIGS. 32A-32D illustrate one embodiment of a subassembly of a conduit graft and annular sewing ring connected together via an intermediate band. The sewing ring 440 desirably has a radial cross-section with a central, generally vertical wall 441, and inner and outer ledges 442a, 442b. A first embodiment of an intermediate band 443 in FIG. 32A includes a generally axial portion 444a and a small lip 444b that projects radially inward. The band 443 conforms to and fits closely against an inner side of the vertical wall 441 of the sewing ring, and the lip 444b rests on the inner ledge 442a. The band 443 is secured to the sewing ring 440 by being insert molded with the inner core, or by ultrasonic or vibration welding to the outer cloth covering. A second embodiment of an intermediate band 445 shown in FIG. 32B includes a generally axial portion 446a and a small lip 446b that projects radially outward and rests on the outer ledge 442b. Again, the band 445 is secured to the sewing ring 440 by being insert molded therewith or by welding.

FIG. 32C shows attachment of a lower end of a conduit graft 447 to the sewing ring 440 and second intermediate band 445. More specifically, a lower collar portion 448 of the graft that extends downward from a seam 449 is ultrasonic or vibration welded to an inner side of the band 445. The finished subassembly is seen in FIG. 32D. This method of attachment can be done with the first embodiment of the band 443 as well, with the collar portion 448 of the graft being located on the inside of the vertical wall 441 of the sewing ring. Both assembly methods eliminate suturing, which speeds up the process. The subassembly can then be independently leak tested before a prosthetic valve is added to form a valved conduit.

FIG. 33A is a perspective exploded view of an alternative configuration of a valved conduit 450 including a conduit graft 452, a prosthetic heart valve 454, and a sewing cuff or ring 456. FIG. 33B illustrates a subassembly of the sewing ring 456 attached to a lower end 458 of the conduit graft 452, with the prosthetic heart valve 454 attached to a holder 460 being lowered into an upper end 462 of the conduit graft. As will be explained in detail below, pre-attachment of the sewing ring 456 to the conduit graft 452 facilitates the assembly process and enables independent leak checking of the graft prior to attachment of the heart valve 454. For the sake of orientation, the sewing ring 456 is deemed to be on a lower end of the graft 452, with the arbitrarily directions up and down defined thereby.

In one embodiment, the sewing ring 456 is the same sewing ring that would normally be attached to the prosthetic heart valve 454. The heart valve 454 includes an internal support frame (not shown) that defines a plurality of alternative commissure posts 470 and cusps 472. The outer edges of three flexible leaflets 474 are secured along the cusps 472 and commissure posts 470 and are supported thereby so as to meet or "coapt" across an outflow end of the valve. The support frame is covered with a biocompatible fabric, and a tubular segment 476 thereof extends downward from the cusps 472. The tubular fabric segment 476 is used to attach the heart valve 454 to the sewing ring 456, as will be shown.

The holder 460 preferably includes a central hub 480 having three legs 482 that radiate outward and are angled downward so as to be able to contact the cusps 472 of the valve 454. The legs 482 of the holder 460 may be sutured to the cloth covering the cusps 472, with the attachments sutures extending back to the central hub 480 to a central cutting well (not shown). In this way, the assembler can deliver the heart valve 454 through the interior of the conduit graft 452, secure it, and use the holder for delivery of the valved conduit 450. In this regard, the holder 460 has sufficient length to extend from the heart valve 454 out of the outflow end of the conduit graft 452. After implanting the valved conduit 450, the surgeon releases the holder 460 from the valve 454 by cutting the attachments sutures (preferably with one cut). Prior to inserting the heart valve 454 into the upper end 462 of the graft 452, the tubular fabric segment 476 is rolled upward and secured with one or more sutures to form a temporary cloth tab 484. This facilitates the passage of the heart valve 454 through the graft 452. Specific steps for attaching the heart valve 454 to the sewing ring 456 are provided below with respect to FIGS. 36-37.

FIGS. 34-35 are a number of steps for pre-assembling the sewing ring 456 to the conduit graft 452. FIG. 34A shows the lower end of the graft 452 within and adjacent to the sewing ring 456. As described previously, the conduit graft 452 comprises an enlarged region or bulge 486 designed to conform to the sinuses of valsalva just above the aortic annulus. In the preferred embodiment, the conduit graft 452 comprises a tubular textile structure, such as Dacron, sealed with a bioresorbable medium. With reference back to FIGS. 33A-33B, a major length 488 of the conduit graft 452 includes a corrugated structure with circumferential grooves 490 that provide lateral flexibility while ensuring that the conduit will not unduly radially compress or expand under the pressure of blood flowing therethrough. The major length 488 is desirably a few centimeters to 10-12 centimeters long. The bulge 486 has corrugations that run longitudinally to enable that region to be radially expanded. A lower collar portion 492 attaches to the bulge 486 at a seam 494. The seam 494 is shown schematically in the sectional views for clarity. As seen in FIG. 33A, the lower collar portion 492 is trimmed and so as to have an undulating shape that matches the undulating shape of the sewing ring 456.

With reference back to FIG. 34A, the sewing ring 456 includes an inner suture-impermeable core 496 surrounded by a biocompatible fabric covering 498. As described previously, the sewing ring 456 desirably has a radial cross-section with a distorted T-shape formed by a central, generally vertical wall 500, an outer flange 502, and an inner ledge 504. Both the outer flange 502 and the inner ledge 504 connect to a lower end of the central vertical wall 500 and project in opposite directions therefrom. The outer flange 502 extends outward at a slight upward angle, and preferably connects to the vertical wall 500 via a series of circumferentially-oriented ribs which define open cells therebetween (such as shown above in FIG. 5). The inner ledge 504 extends generally radially inward and has no such ribs. As mentioned, the sewing ring 456 desirably has an undulating shape with alternating peaks and valleys that ultimately correspond to features on the prosthetic heart valve 454. The lower collar portion 492 of the conduit graft 452 extends within the vertical wall 500 and inward along the inner ledge 504. The termination of the collar portion 492 conforms closely with the undulating shape of the inner ledge 504.

Figure 34A:
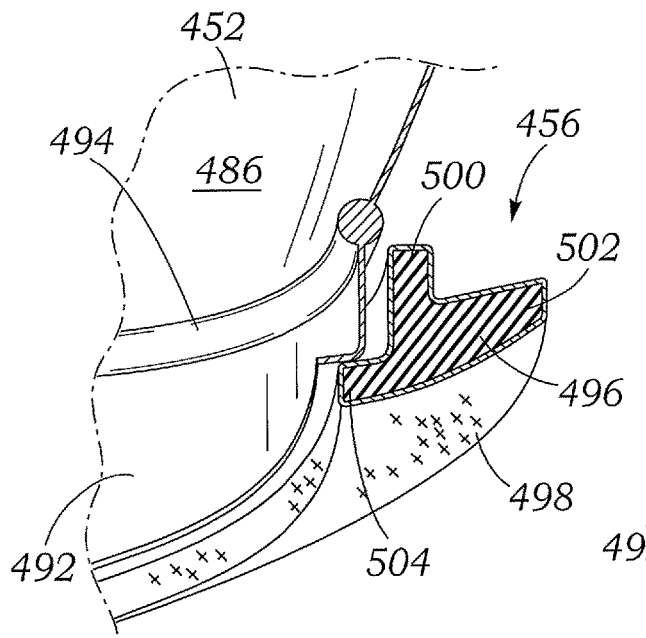
FIGS. 34A-34D are sectional and perspective views of several initial steps in the pre-assembly of the sewing ring to the conduit graft of FIGS. 33A-33B.
Figure 34B:
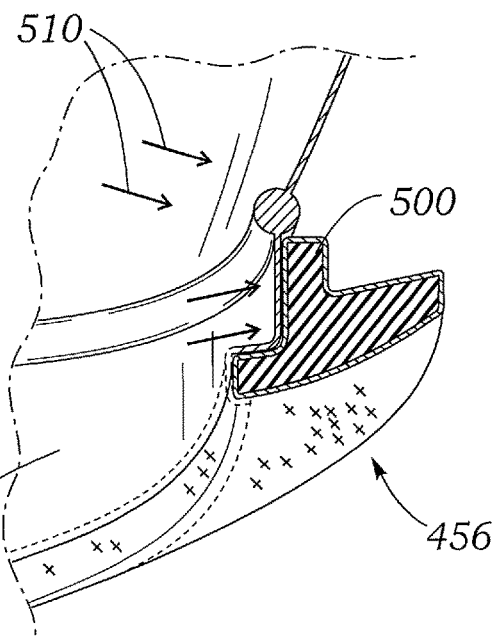

FIG. 34B shows a number of outward force arrows 510 directed to the inside of the conduit graft 452. These force arrows 510 represent the force that would be applied by a rigid mandrel (similar to that shown in FIG. 35B) inserted within the conduit graft 452. Desirably, the mandrel is large enough so as to slightly expand the flexible sewing ring 456. FIG. 34B also indicates in phantom an extension of the collar portion 492 so that it wraps around the inner end of the inner ledge 504 of the sewing ring 456, which may help seal the border between the graft 452 and sewing ring.

Figure 34C:
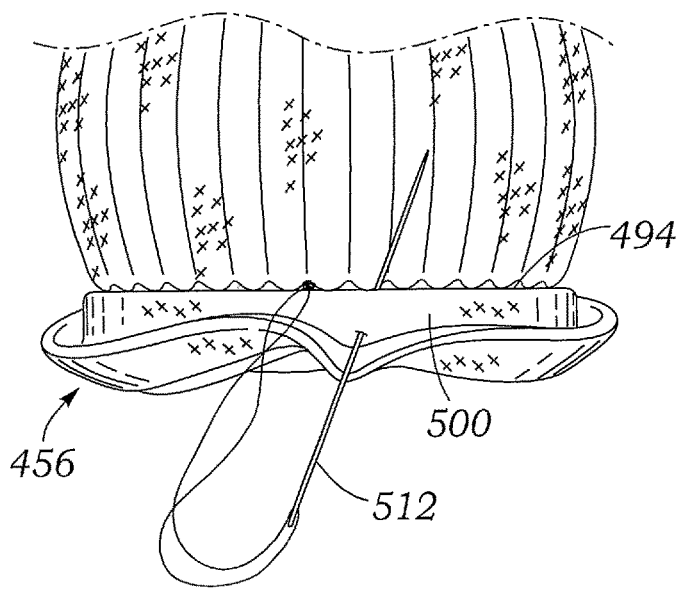
Figure 34D:
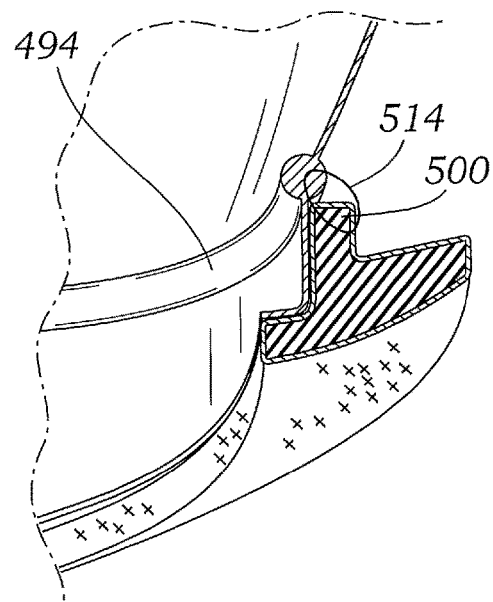

FIG. 34C shows the process of forming a seam along the upper edge of the sewing ring 456, connecting it with the conduit graft 452. In particular, a needle 512 passes through the vertical wall 500 and through the seam 494 of the conduit graft 452. One of the stitches 514 is shown at the desired location in FIG. 34D. A series of the stitches 514 are sewn around the circumference between the conduit graft 452 and sewing ring 456 to form a seam. Preferably, the needle 512 does not pierce the wall of the conduit graft 452 so as to minimize blood leakage therethrough.

Figure 35A:
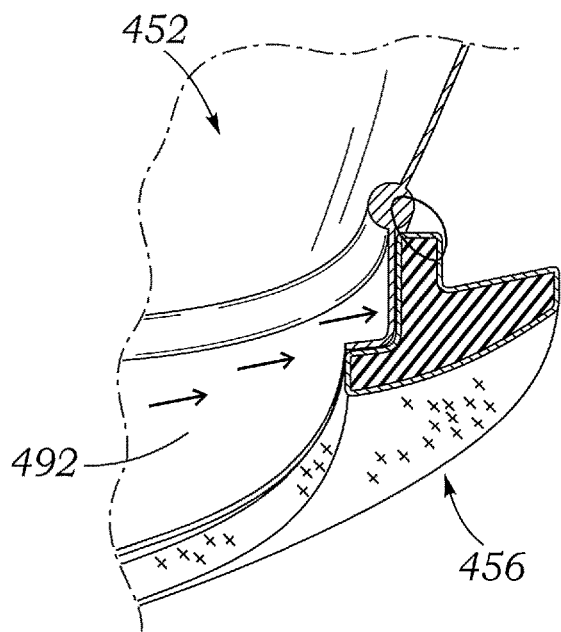
FIGS. 35A-35C are sectional and perspective views of several further steps in the pre-assembly of the sewing ring to the conduit graft of FIGS. 33A-33B.
Figure 35C:
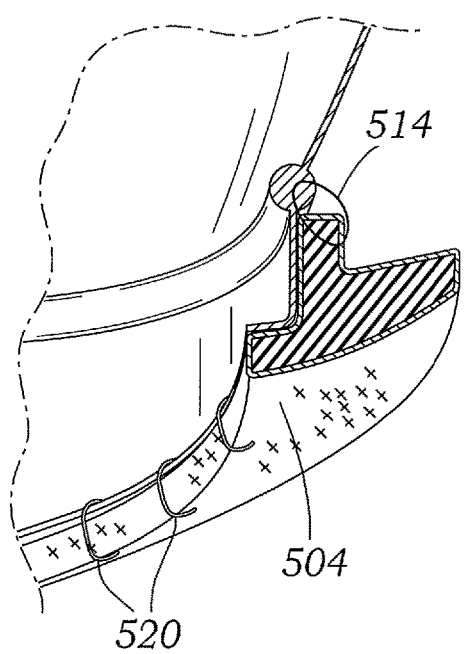
Figure 35B:
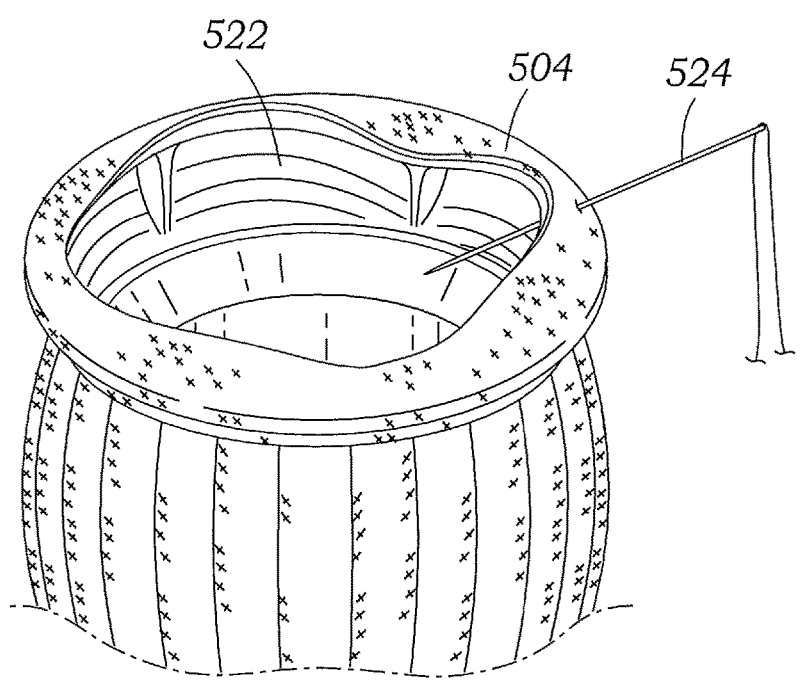

FIGS. 35A-35C illustrate the process of forming a second seam comprising a plurality of stitches 520 between the conduit graft 452 and sewing ring 456. In particular, a mandrel 522 seen in the upside-down view of FIG. 35B again applies an outward force on the collar portion 492 against the inside of the sewing ring 456. Once again, the mandrel 522 is preferably large enough so as to slightly outwardly stretch the sewing ring 456. Another needle 524 is then used form the stitches 520 between the terminal end of the collar portion 492 and the inner edge of sewing ring inner ledge 504. In one embodiment, the mandrel 522 is segmented at the uppermost end as seen in FIG. 35B so as to provide a series of gaps around the circumference through which the needle 524 can be passed. This provides a guide to where the stitches 520 are placed. The series of stitches 520 as seen in FIG. 35C forms a lower seam between the conduit graft 452 and sewing ring 456 and completes the subassembly. The mandrel 522 is then removed.

At this point, the completed subassembly of the conduit graft 452 and sewing ring 456 can be independently leak tested. More particularly, a leak test with the same fluid media that the maker of conduit graft 452 uses can be done. Pulsatile testing with saline is commonly done for such grafts. This is not possible once the heart valve 454 has been incorporated. If necessary, additional coatings (silicone, gelatin, hydrogel, etc.) to seal the holes caused by forming the stitches can be applied without fear of exposing the heart valve 454 and its bioprosthetic leaflets 474.

Another advantage of separating the sewing ring 456 from the remainder of the prosthetic heart valve 454 is the ability to customize each valved conduit 450. More particularly, for many commercial heart valves the majority of the valve components across all models are the same, and it is the sewing ring that differentiates them. Different heart valve models can thus be coupled to the same subassembly of the sewing ring 456 and conduit graft 452. This is a much more flexible manufacturing process and inventory control. Moreover, without the sewing ring 456 attached, the number of fixtures needed to do flow and leak testing of the valve 454 is simplified. Current valve flow and leak testers have different fixtures for all of the valve models to conform to the different sewing ring geometries. By removing the sewing ring 456, all of the prosthetic heart valves configured as in FIG. 33A would have the same "temporary" cloth sewing ring and therefore only one fixture for each size would be needed.

Most of the leakage around valved conduits appears to occur around the interface between the valve sewing ring and the graft. When the conduit graft is attached to inflow of the valve skirt, this allows for a high leak rate due to the higher porosity of the stent cloth used to cover the heart valve. A lower leak rate can be achieved by attaching denser graft cloth over the sewing ring and eliminating the leakage along the inflow edge. As stated, the conduit grafts described herein comprise a tubular textile structure, such as Dacron, sealed with a bioresorbable medium such as gelatin or collagen, while the stent cloth most used to cover the heart valve is uncoated fabric such as polyethylene terephthalate (PET).

FIGS. 36A-37C help illustrate a number of steps that can be used for pre-assembling the sewing ring 456 to the conduit graft 452 in which denser graft cloth is wrapped over and secured to the sewing ring. As the assembly is similar to the one described above, like parts will be given like numbers.

Figure 36A:
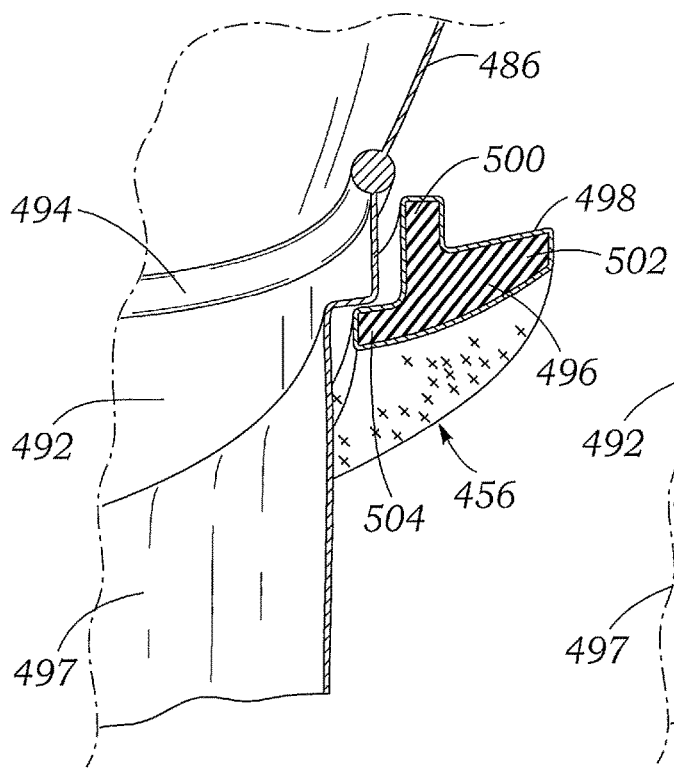
FIGS. 36A-36D are sectional and perspective views of alternative initial steps in the pre-assembly of the sewing ring to the conduit graft of FIGS. 33A-33B.

FIG. 36A shows the lower end of the graft 452 within and adjacent to the sewing ring 456. The conduit graft 452 comprises an enlarged region or bulge 486 designed to conform to the sinuses of valsalva just above the aortic annulus. As explained above with reference to FIG. 33A, a major length 488 of the conduit graft 452 can include a corrugated structure with circumferential grooves 490 that provide lateral flexibility while ensuring that the conduit will not unduly radially compress or expand under the pressure of blood flowing therethrough. The major length 488 can desirably be a few centimeters to 10-12 centimeters long. The bulge 486 can have corrugations that run longitudinally to enable that region to be radially expanded. A lower collar portion 492 can be attached to the bulge 486 at a seam 494. The lower collar portion 492 in one construction extends downwardly in a skirt 497 that is initially draped through the orifice defined by the annular sewing ring 456.

Desirably, the sewing ring 456 can include an inner suture-impermeable core 496 surrounded by a biocompatible fabric covering 498. The core 496 can desirably have a radial cross-section with a distorted T-shape formed by a central, generally vertical wall 500, an outer flange 502, and an inner ledge 504. One preferred shape of the core 496, and thus the sewing ring 456, has been described above. Also, the lower collar portion 492 of the conduit graft 452 can extend within the vertical wall 500 and inward along the inner ledge 504, and the skirt 497 can continue downward past the inner ledge 504.

Figure 36B:
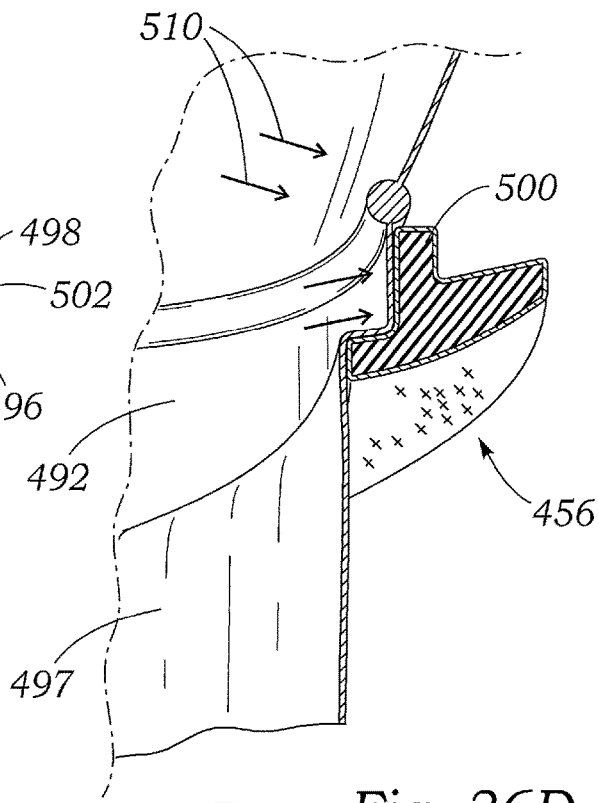

FIG. 36B shows a number of outward force arrows 510 directed to the inside of the conduit graft 452. These force arrows 510 represent the force that would be applied by a rigid mandrel (similar to that shown in FIG. 35B) inserted within the conduit graft 452. Desirably, the mandrel is large enough so as to slightly expand the flexible sewing ring 456.

Figure 36C:
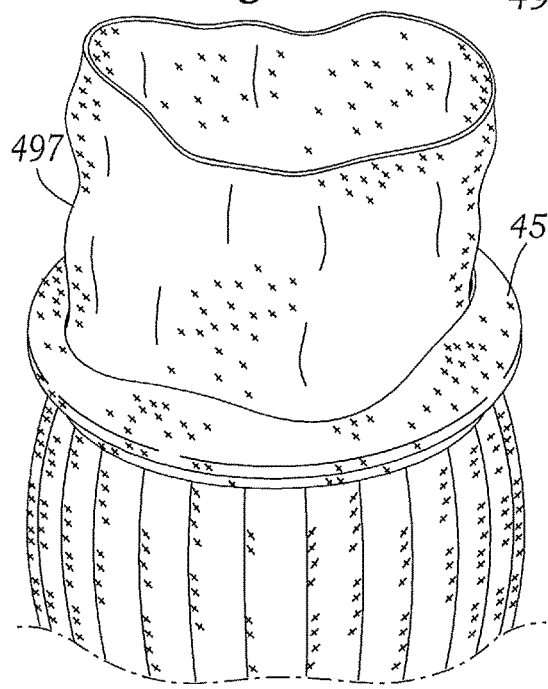

FIG. 36C shows the partially assembled sewing ring 456 and conduit graft 452 in an inverted orientation, illustrating the tubular skirt 497 that extends through and past the sewing ring. In one construction, the skirt 497 of the conduit graft 452 is secured to an underside of the sewing ring 456, and preferably underneath the fabric-covered outer flange 502 of the core 496. To do this, the tubular skirt 497 can be segmented to enable folding outward without puckering or stretching.

Figure 36D:
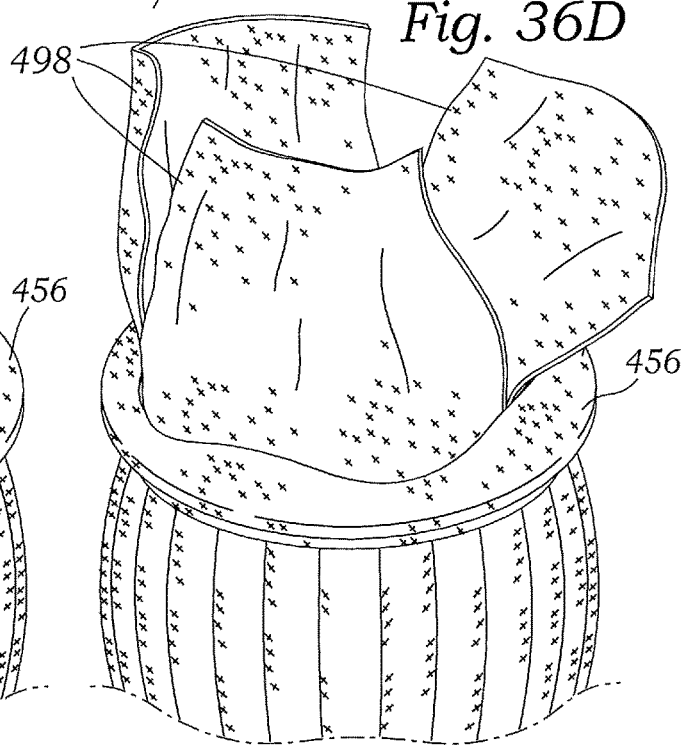

FIG. 36D illustrates three cuts or slits formed in the tubular skirt 497 from its terminal edge to approximately the intersection with the sewing ring 456, in particular the fabric-covered inner ledge 504. The slits segment the tubular skirt 497 into multiple generally rectangular segments 498. Three slits and segments 498 are shown, though more than three may be created. In one configuration, three V-shaped "darts" are cut into the tubular skirt 497 from its terminal edge to approximately the intersection with the sewing ring 456, like the slits shown. The segments 498 formed by cutting darts are thus more trapezoidal than rectangular, narrowing as they extend toward their terminal edges.

Figure 37A:
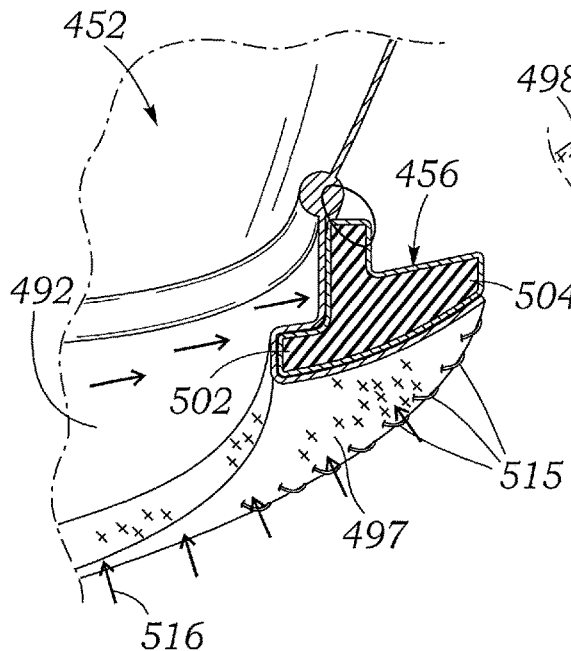
FIGS. 37A-37C are sectional and perspective views of several further steps in the pre-assembly of the sewing ring to the conduit graft of FIGS. 33A-33B.

Once segmented, the tubular skirt 497 is wrapped under the sewing ring 456, trimmed to match the radial dimension of the sewing ring, and secured with a series of stitches 515 at the outer edge of the outer flange 502 of the core 496, as seen in FIG. 37A. Although not shown, an additional seam can be added through the skirt 497 and inner ledge 504. During the process the outward force imparted by the mandrel can be maintained, and an additional upward force as shown by arrows 516 can be applied to the underside of the sewing ring 456 to keep the skirt 497 taut. Such a force 516 can be applied using a mandrel, or clamps or pins or other such temporary holders can be used.

Figure 37C:
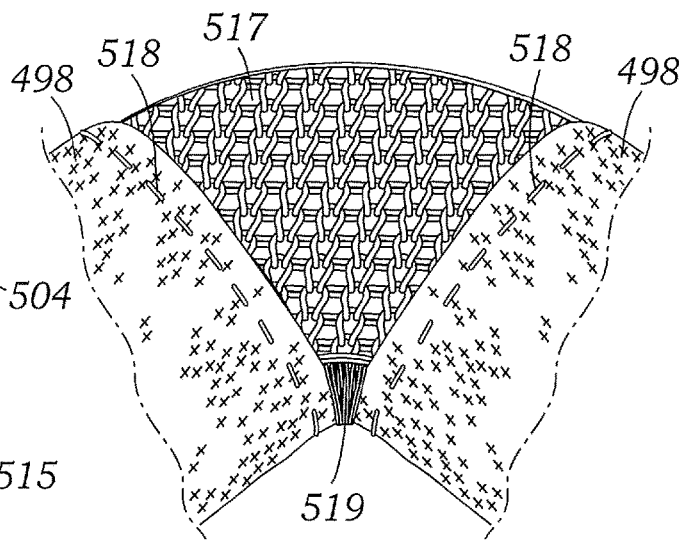
Figure 37B:
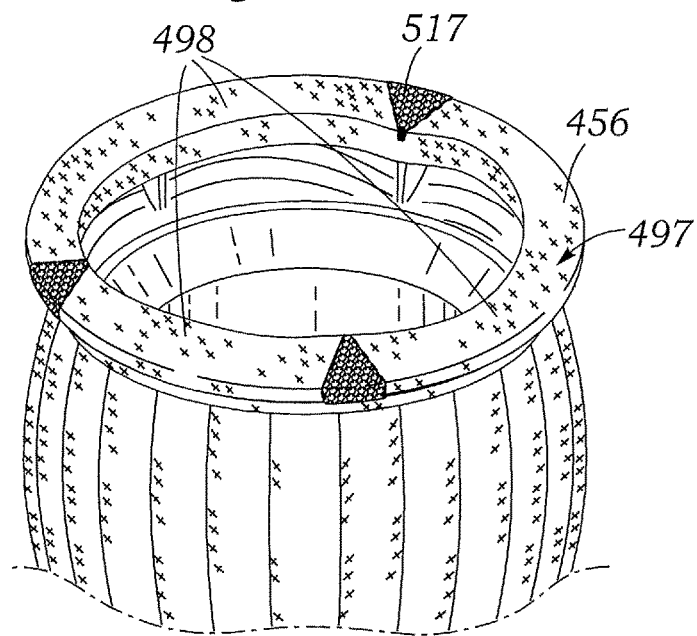

FIG. 37B shows the completed assembly of the conduit graft 452 and sewing ring 456, with the three segments 498 of the skirt 497 wrapped under and sewn to the sewing ring. By virtue of the annular shape of the sewing ring 456, the three segments 498 separate as they extend outward under the sewing ring and form three triangular gaps 517 on the underside of the sewing ring.

FIG. 37C is an enlargement of one of the triangular gaps 517 showing further radial seams 518 stitched along the lateral edges of each of the adjacent segments 498, in a V-shaped pattern. Additionally, the point at which the segments 498 diverge at the inner ledge 504 of the sewing ring 456 is reinforced with concentrated stitching 519. These stitches help prevent leakage past the severed junction where the segments 498 diverge, and between the sewing ring 456 and the conduit graft 452, and of course provides structural reinforcement to the cut edges to eliminate fraying.

Again, the completed subassembly of the conduit graft 452 and sewing ring 456 can then be independently leak tested. As stated above, pulsatile testing with saline is commonly done for such grafts. Further, additional coatings (silicone, gelatin, hydrogel, etc.) to seal the holes caused by forming the stitches can be applied without fear of exposing the heart valve 454 and its bioprosthetic leaflets 474. By wrapping the denser conduit graft 452 fabric skirt 497 under the sewing ring 456, a better barrier against blood leakage is provided and blood leakage is further inhibited or prevented.

FIG. 38A illustrates the prosthetic heart valve 454 connected to the holder 460 within the lower end of the subassembly of the conduit graft 452 and sewing ring 456 cut away. As mentioned above, the assembler advances the valve 454 through the subassembly until a lower or inflow end of the valve 454 aligns with the sewing ring inner ledge 504, as indicated by a comparison of FIGS. 38B and 38D. The holder 460 can be removed at this point, but is preferably left in place during the subsequent sewing steps and used for delivery of the valved conduit 450.

The heart valve 454 desirably has an inner leaflet support frame covered with fabric that defines a flow orifice, such as described above with respect to FIG. 4A. Again, the inner support frame preferably includes a stent with two concentric bands that are enclosed in fabric which is bunched or rolled into an outwardly-directed sewing tab. The outer edges of the leaflets are sandwiched between the top of the stent structure and the bottom of a cloth-covered wireform that may have a sewing flap as shown. Of course, this particular type of heart valve is representative of many others.

FIG. 38C shows the unfinished assembly upside-down with the tubular fabric segment 476 extending beyond the sewing ring 456. A needle 530 is shown passing a suture through the fabric segment 476 and the inner ledge 504 of the sewing ring 456. The positioning of stitches 532 between these two components is seen in FIG. 38D.

Figure 39A:
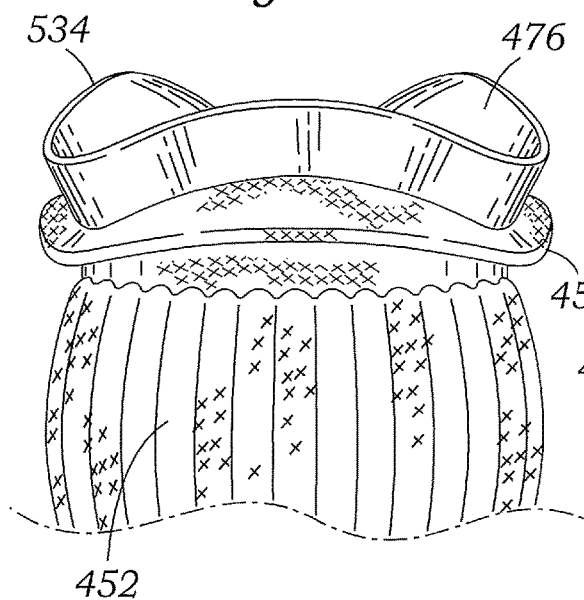
FIGS. 39A-39D are perspective and sectional views of several final steps for forming the valved conduit system of FIG. 33A.
Figure 39B:
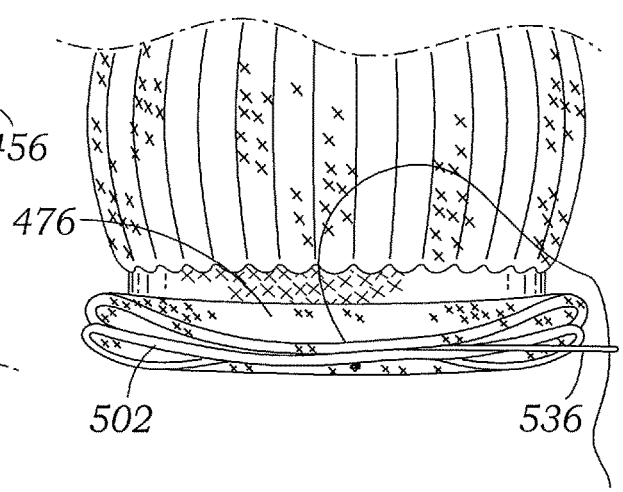
Figure 39C:
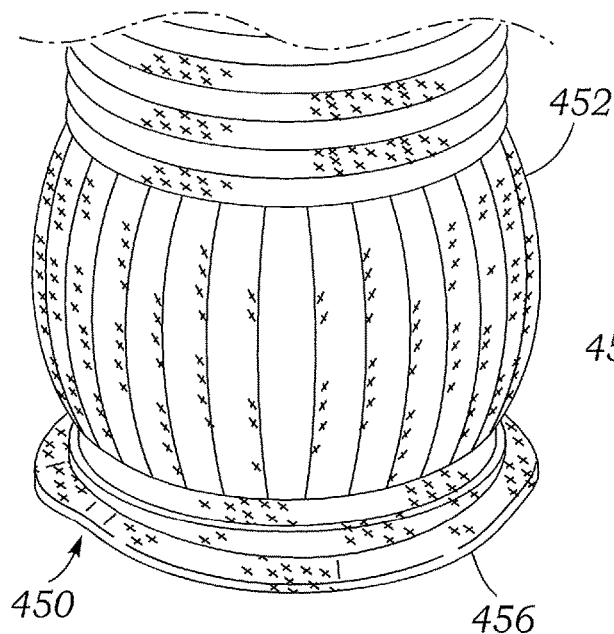
Figure 39D:
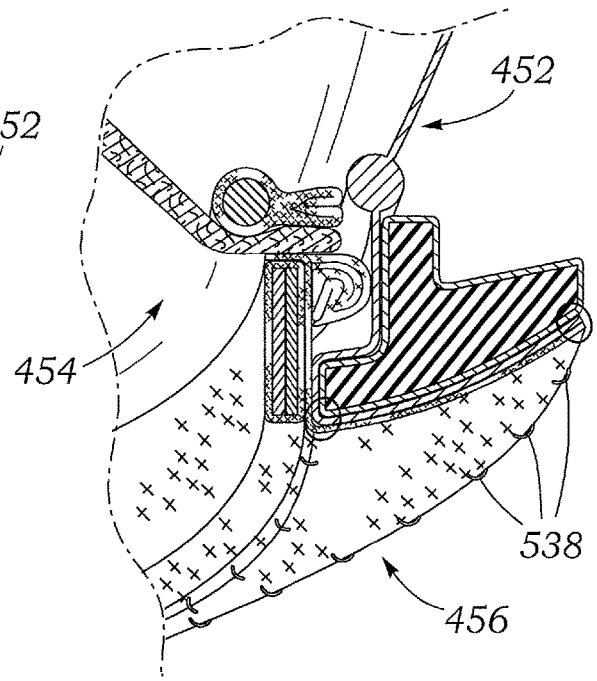

FIGS. 39A-39D illustrate formation of a second seam between the conduit subassembly and the heart valve 454. First, as seen in FIG. 39A, excess tubular cloth from the fabric segment 476 is trimmed and/or folded to create an even edge 534. The assembler then folds the fabric segment 476 against the underside of the sewing ring 456, and preferably against the fabric skirt 497 as seen in FIG. 38D. Temporary means for holding the fabric segment 476 flush against the sewing ring 456, such as pins or the like, may be used. FIG. 39B shows a needle 536 passed through the outermost edges of the outer flange 502 of the sewing ring 456 and the fabric segment 476 creating a series of stitches 538 that together define a seam, as best seen in FIG. 39D. The lower end of the finished valved conduit 450 is shown in FIG. 39C.

The valved conduit 450 with the holder 460 attached to the valve 454 is then packaged in a sterile container and stored until needed. As mentioned above, the heart valve 454 is desirably a "dry" valve that can be stored with a conduit graft 452 sealed with a bioresorbable medium such as gelatin or collagen. This process produces a valved conduit that is ready for implantation without the need for a clinical rinse in saline, thereby shortening implant time. Furthermore, the handle 460 remains attached and is thus ready to use during the implant procedure. Preferably the handle 460 has a length sufficient to extend out of the top end of the conduit graft 452. The surgeon manipulates the valved conduit 450 into place using the handle 460, and secures the sewing cuff 418 of the valve to the annulus. At any time, the holder 460 can be removed to help with visibility of the interior of the valve 454.

Figure 40:
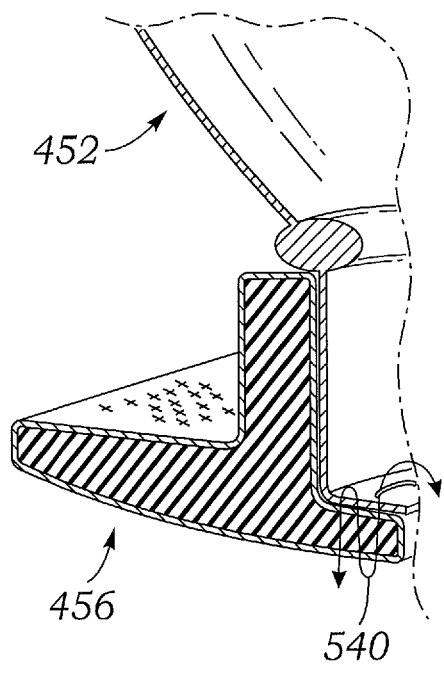
FIG. 40 shows an alternative type of stitch that may be used between the conduit graft and sewing ring.

FIG. 40 shows an alternative type of stitch that may be used between the conduit graft 452 and sewing ring 456. Desirably, whip stitches 520 as shown in FIG. 35C are used due to the ease of assembly. Alternatively, a manual in-and-out stitch 540 as shown in FIG. 40 may be used. Furthermore, an in-and-out stitch 540 can be applied by an automated or robotic sewing machine.

Figure 41:
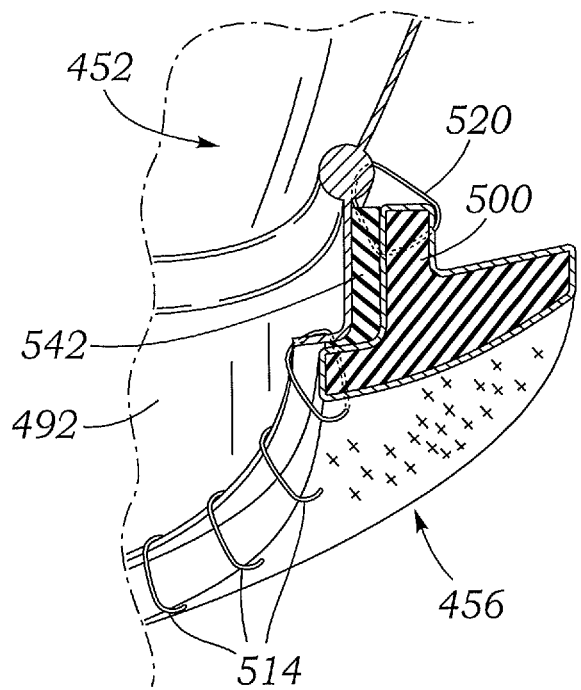
FIG. 41 shows the addition of a sealant that may be used between the conduit graft and sewing ring.

FIG. 41 shows the addition of a sealant 542 interposed between the conduit graft 452 and sewing ring 456. As mentioned, a sealant such as silicone or adhesive can be used in various places between the components of the valve conduit 450, but an especially important location is between the collar portion 492 of the conduit graft 452 and the vertical wall 500 of the sewing ring 456. Although both stitches lower and upper stitches 514 and 520 are shown in FIG. 41, it should be understood that one or even both of them may be omitted if a suitable adhesive is used between the opposing surfaces.

Figure 42A:
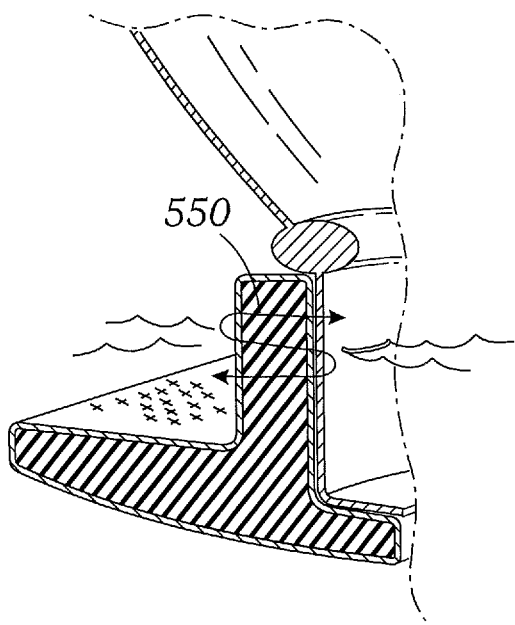
FIGS. 42A and 42B show alternative stitches that may be used between the conduit graft and sewing ring.
Figure 42B:
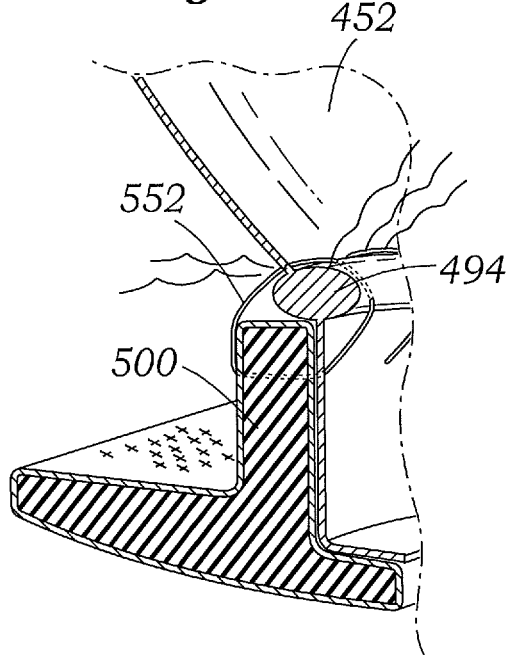

FIGS. 42A and 42B show still further alternative stitches that may be used between the conduit graft 452 and sewing ring 456. First, FIG. 42A indicates a radial in-and-out stitch 550 at the location of the vertical wall 500 of the sewing ring 456. Although this stitch is an alternative, it may provide an avenue for leakage as indicated and preferably is used in conjunction with a sealant or adhesive between the two surfaces. Likewise, FIG. 42B illustrates a stitch 552 at the top of the vertical wall 500 that penetrates through the conduit graft 452, as opposed to just through the seam 494. Penetrating the conduit graft 452 introduces an avenue for leakage, and thus this type of stitch 552 should be used in conjunction with a sealant.

Figure 44:
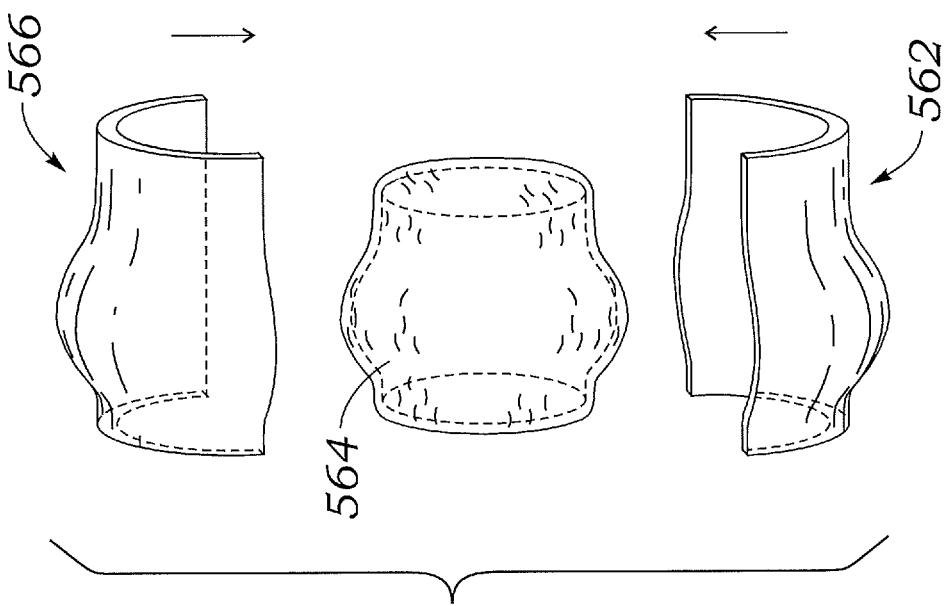
FIGS. 43 and 44 schematically illustrate a process for shaping tissue to form an aortic root portion of a conduit graft for use in the combinations herein.
Figure 43:
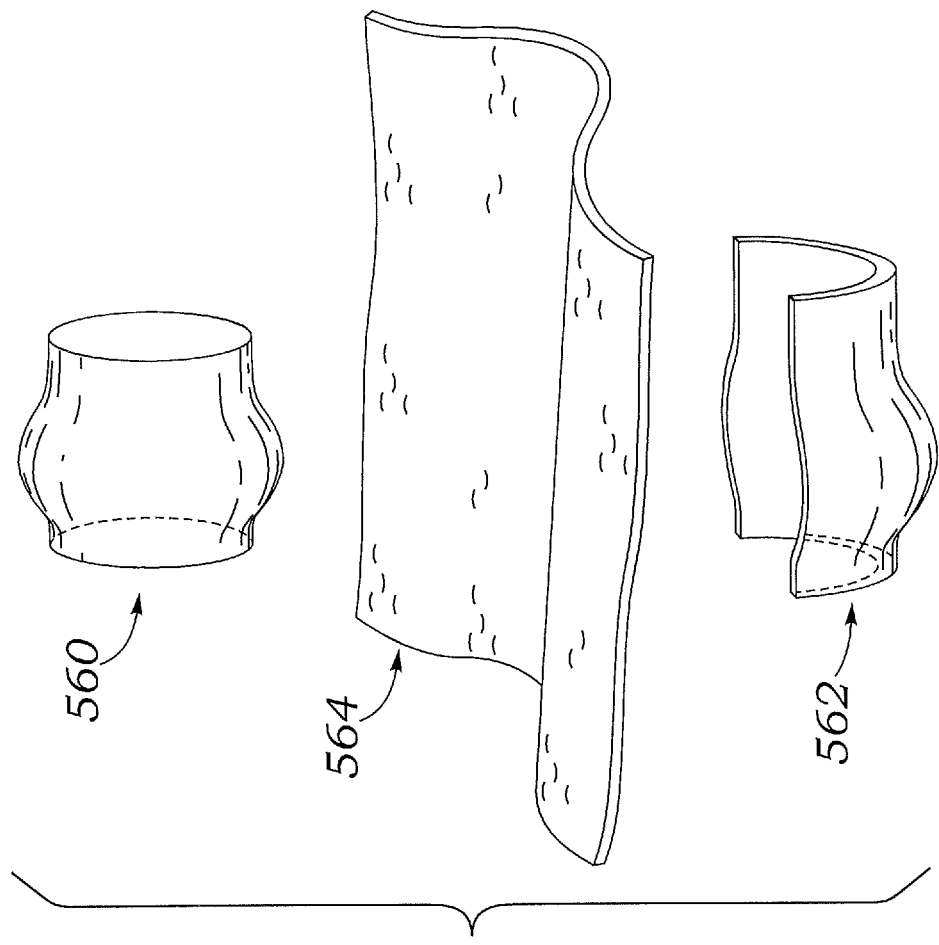

FIGS. 43 and 44 schematically illustrate a process for shaping tissue to form an aortic root portion of a conduit graft. Fabric grafts present relatively large surface area of biomaterial in contact with blood. Sometimes this fabric is never completely covered with pannus resulting in need for anticoagulant therapy for many patients. Moreover, fabric conduits tend to seep plasma until clotted. One possible solution is to form the graft from tissue, minimizing thrombolysis and thromboembolism and reducing seepage. For example, the tissue sheet may be formed into a tube or other graft shape to replace the conduit graft described herein.

Moreover, the tissue graft may be shaped to provide the sinus portion of the ascending aortic graft. For example, an inner mandrel 560 may be combined with an outer mold half 562 as seen in FIG. 43 to sandwich therebetween a sheet of tissue 564. The tissue is wrapped around the inner mandrel 560, and then upper half 566 of the mold is combined as in FIG. 44. The mold assembly is shaped to reflect the desired final geometry of the tissue, such as to replicate the geometry of the aortic root complete with sinuses. The mold and tissue are placed into a fixative solution (glutaraldehyde, formaldehyde, etc.) for fixation. If necessary, the fixation fluid can be pressurized to facilitate diffusion through the tissue and mold. After fixation, the sheet of tissue 564 may be sewn into a tube and other necessary structures attached, such as sewing cuffs. Various types of tissue can be used, including human or animal pericardium, dura mater, fascia latta, or other such sheet tissue.

The tissue graft described above can be supplied wet, stored in glutaraldehyde, or can be dried as described herein. A dry sinus graft would enhance handling, eliminate the need for extended rinsing, and certain treatments will reduce the risk of calcification in the graft component.

One aspect of the present application provides techniques for coupling implantable valves with conduits, and in particular bioprosthetic heart valves that have been dried and are not stored immersed in a preservative solution. The term "dried" or "dry" bioprosthetic heart valves refers in general to the ability to store those heart valves without immersion in solution (e.g., a preservative like glutaraldehyde), and in particular to dry storage for extended periods without degradation of functionality of the bioprosthetic valve. There are a number of proposed methods for drying bioprosthetic heart valves, and for drying tissue implants in general, and the present application encompasses bioprosthetic heart valves that are processed by any of these methods.

One strategy for drying tissue is to dehydrate the bioprosthetic tissue in a glycerol/ethanol mixture, sterilize with ethylene oxide, and package the final product "dry." This process eliminates the potential toxicity of glutaraldehyde as a sterilant and storage solution. There have been several methods proposed to use sugar alcohols (i.e., glycerine), alcohols, and combinations thereof as post-glutaraldehyde processing methods so that the resulting tissue is in a "dry" state rather than a wet state with excess glutaraldehyde. Glycerol-based methods can be used for such storage, such as described in Parker et al. (Thorax 1978 33:638). A particularly preferred method of drying bioprosthetic heart valves is disclosed in U.S. Pat. No. 8,007,992 to Tian, et al. (the disclosure of which is expressly incorporated herein by reference) wherein fixed tissue is treated with a non-aqueous mixture of glycerol and $C_1$-$C_3$ alcohol selected from the group consisting of methanol, ethanol, n-propanol, 2-propanol. Likewise, U.S. Pat. No. 6,534,004 (Chen et al.) describes the storage of bioprosthetic tissue in polyhydric alcohols such as glycerol. In processes where the tissue is dehydrated in an ethanol/glycerol solution, the tissue may be sterilized by ethylene oxide (ETO), gamma irradiation, or electron beam irradiation.

More recently, Dove, et al. in U.S. Pat. No. 7,972,376, issued Jul. 5, 2011, propose solutions for certain detrimental changes within dehydrated tissue that can occur as a result of oxidation, the disclosure of which is expressly incorporated herein by reference. Dove, et al. propose permanent capping of the aldehyde groups in the tissue (reductive amination). One preferred anticalcification tissue treatment includes applying a calcification mitigant such as a capping agent or an antioxidant to the tissue to specifically inhibit oxidation in dehydrated tissue and reduce in vivo calcification. The treatment specifically caps aldehyde groups in crosslinked (e.g., with glutaraldehyde) bovine, porcine, or equine pericardial tissue or a porcine valve. In one method, tissue leaflets in assembled bioprosthetic heart valves are pretreated with an aldehyde capping agent prior to dehydration and sterilization. Dove, et al. also describe the addition of chemicals (e.g. antioxidants) to the dehydration solution (e.g., ethanol/glycerol) to prevent oxidation of the tissue during sterilization (ethylene oxide, gamma irradiation, electron beam irradiation, etc.) and storage. The capping process uses an amine, for example ethanolamine or lysine, and a reducing agent, followed by final processing with glycerol and an alcohol. The capping agent may be selected from the group consisting of: an amine, an amino acid, and an amino sulfonate. The reducing agent may be a borohydride, for example sodium borohydride or cyanoborohydride. Other reducing agents include: sodium bisulfite+acetylacetone, and formic acid+formaldehyde.

These and other methods for drying bioprosthetic heart valves are used prior to coupling of the valve with the conduit. The removal of a percentage of water from the valve and replacement with glycerol and ethanol allows the device to be stored "dry" (i.e. glycerolized). The "dry" valve may then be sewn into the polyester or tissue conduit or graft and be ready for implantation. This process allows making a valved conduit that is ready for implantation without the need for a clinical rinse in saline, thereby shortening implant time. For purpose of definition, a "dry" bioprosthetic tissue is one with less than 70% water content. In terms of practical rehydration, functional valves have at least 70% water content. The most important distinction of "dry" valves (or tissue therein), however, is that they may be stored dry for extended periods (sometimes years) without degradation of functionality of the valve.

A number of exemplary bioprosthetic heart valves and conduits are shown and described in the present application. Each of these different types of heart valves may be processed so that they are stored dry. The reader will understand that the present methodologies apply to any and all bioprosthetic valves that are stored dry, and are not limited to those exemplary valves shown herein. In particular, prosthetic heart valves for implant at any of the four native valve annuluses—aortic, mitral, pulmonary, and tricuspid—may be dried and stored in accordance with the principles described herein. Alternatively, valved conduits produced in accordance with the principles disclosed herein may be used in locations other than heart valve replacement, such as venous valves by connecting a small bileaflet valve to or within a small diameter conduit.

Additionally, a number of techniques for packaging the dry bioprosthetic heart valves and their delivery systems are possible. In general, a bioprosthetic heart valve must be stored in sterile conditions, which requires at least one sterile container. Preferably, however, a dual-barrier packaging system is used to reduce the chance of contamination of the implant at the time of surgery. For instance, U.S. Patent Publication No. 2011/0147251 to Hodson, et al. discloses exemplary packaging systems which can be utilized, the contents of which are hereby expressly incorporated herein.

The present application describes systems and methods for pre-assembling and storing a bioprosthetic heart valve and conduit to form the valved conduit. The term "pre-assembling" or "pre-assembled" refers to connection of the heart valve and conduit prior to the operating room technicians opening the sterile packaging. In other words, the valved conduit emerges mechanically assembled from the packaging, substantially ready for delivery (after any pre-surgery washing or other such preparation).

While the invention has been described in its preferred embodiments, it is to be understood that the words which have been used are words of description and not of limitation. Therefore, changes may be made within the appended claims without departing from the true scope of the invention.

What is claimed is:

1. A valved conduit, comprising:
   a subassembly of:
      a conduit graft comprising a longitudinal tubular portion between an upper end and a lower end, the lower end having a collar portion; and
      an annular sewing ring comprising an inner core and an outer fabric covering, the sewing ring being positioned adjacent the lower end of the conduit graft whereby the collar portion contacts an inner wall of the sewing ring and the collar portion is secured to the sewing ring, wherein the conduit graft is secured to the sewing ring using sutures, and wherein the collar portion of the conduit graft has a skirt that extends through the annular sewing ring and is cut into segments that are wrapped underneath and secured to the sewing ring with sutures;
   a prosthetic heart valve having an inner support frame covered with fabric and defining a flow orifice and a plurality of leaflets extending inward from the support frame to ensure one-way blood flow through the heart valve, wherein the heart valve is positioned within the lower end of the conduit graft and the fabric covering the support frame extends downward in a tubular segment and is folded radially outward underneath the subassembly of the conduit graft and sewing ring and secured thereto with sutures;
a holder attached to the heart valve and extending from the heart valve out of the upper end of the conduit graft.

2. The valved conduit of claim 1, wherein the collar portion has an undulating shape around its circumference with peaks and valleys, and the sewing ring also has an undulating shape around its circumference with peaks and valleys, wherein the peaks and valleys of the collar portion align with the peaks and valleys of the sewing ring.

3. The valved conduit of claim 1, wherein the conduit graft is secured to the sewing ring using an intermediate band which is secured to both the conduit graft and sewing ring.

4. The valved conduit of claim 1, wherein the heart valve leaflets are made of bioprosthetic tissue.

5. The valved conduit of claim 4, wherein the conduit graft comprises a tubular matrix impregnated with gelatin.

6. The valved conduit of claim 5, further including an additional coating selected from the group consisting of silicone, gelatin, and hydrogel applied to the subassembly.

7. The valved conduit of claim 4, wherein the heart valve leaflets are formed of bovine pericardium that has been cross-linked using glutaraldehyde or other aldehyde containing agents, treated with a capping agent, and is dehydrated with a glycerol solution.

8. A valved conduit, comprising:
a conduit graft comprising a longitudinal tubular portion between an upper end and a lower end, the lower end having a collar portion;
an annular sewing ring comprising an inner core and an outer fabric covering, the sewing ring being positioned adjacent the lower end of the conduit graft whereby the collar portion contacts an inner wall of the sewing ring and the collar portion is secured to the sewing ring; and
a prosthetic heart valve having an inner support frame covered with fabric and defining a flow orifice and a plurality of leaflets extending inward from the support frame to ensure one-way blood flow through the heart valve, the heart valve having no sewing ring, wherein the heart valve is positioned within the lower end of the conduit graft and the fabric covering the support frame extends downward in a tubular segment and is folded radially outward underneath the subassembly of the conduit graft and sewing ring and secured thereto with sutures.

9. The valved conduit of claim 8, wherein the collar portion has an undulating shape around its circumference with peaks and valleys, and the sewing ring also has an undulating shape around its circumference with peaks and valleys, wherein the peaks and valleys of the collar portion align with the peaks and valleys of the sewing ring.

10. The valved conduit of claim 8, wherein the collar portion of the conduit graft has a skirt that extends through the annular sewing ring and is cut into segments that are wrapped underneath and secured to the sewing ring.

11. The valved conduit of claim 8, wherein the conduit graft is secured to the sewing ring by welding.

12. The valved conduit of claim 8, wherein the conduit graft is secured to the sewing ring using an intermediate band which is secured to both the conduit graft and sewing ring.

13. The valved conduit of claim 8, wherein the heart valve leaflets are made of bioprosthetic tissue.

14. The valved conduit of claim 13, wherein the conduit graft comprises a tubular matrix impregnated with gelatin.

15. The valved conduit of claim 14, further including an additional coating selected from the group consisting of silicone, gelatin, and hydrogel applied to the subassembly.

16. The valved conduit of claim 13, wherein the heart valve leaflets are formed of bovine pericardium that has been cross-linked using glutaraldehyde or other aldehyde containing agents, treated with a capping agent, and is dehydrated with a glycerol solution.

17. The valved conduit of claim 8, further including a holder attached to the heart valve and extending from the heart valve out of the upper end of the conduit graft, wherein the holder includes a central hub and three legs that radiate outward and are angled downward, the prosthetic heart valve support frame defining three undulating cusps and commissures, with the legs of the holder contact being secured to the three cusps.

18. A valved conduit, comprising:
a subassembly of:
a conduit graft comprising a tubular matrix impregnated with gelatin and having a longitudinal tubular portion between an upper end and a lower end, the lower end having a collar portion; and
an annular sewing ring comprising an inner core and an outer fabric covering, the sewing ring being positioned adjacent the lower end of the conduit graft whereby the collar portion contacts an inner wall of the sewing ring and the collar portion is secured to the sewing ring,
wherein the subassembly includes an additional coating selected from the group consisting of silicone, gelatin, and hydrogel;
a prosthetic heart valve having an inner support frame covered with fabric and defining a flow orifice and a plurality of leaflets made of bioprosthetic tissue extending inward from the support frame to ensure one-way blood flow through the heart valve, wherein the heart valve is positioned within the lower end of the conduit graft and the fabric covering the support frame extends downward in a tubular segment and is folded radially outward underneath the subassembly of the conduit graft and sewing ring and secured thereto with sutures;
a holder attached to the heart valve and extending from the heart valve out of the upper end of the conduit graft.

19. The valved conduit of claim 18, wherein the collar portion has an undulating shape around its circumference with peaks and valleys, and the sewing ring also has an undulating shape around its circumference with peaks and valleys, wherein the peaks and valleys of the collar portion align with the peaks and valleys of the sewing ring.

20. The valved conduit of claim 18, wherein the conduit graft is secured to the sewing ring using sutures.

21. The valved conduit of claim 18, wherein the conduit graft is secured to the sewing ring by welding.

22. The valved conduit of claim 18, wherein the conduit graft is secured to the sewing ring using an intermediate band which is secured to both the conduit graft and sewing ring.

23. The valved conduit of claim 18, wherein the heart valve leaflets are formed of bovine pericardium that has been cross-linked using glutaraldehyde or other aldehyde containing agents, treated with a capping agent, and is dehydrated with a glycerol solution.

* * * * *